US011180773B2

(12) United States Patent
Cordova-Kreylos et al.

(10) Patent No.: US 11,180,773 B2
(45) Date of Patent: Nov. 23, 2021

(54) *CHROMOBACTERIUM SUBTSUGAE* GENES

(71) Applicant: MARRONE BIO INNOVATIONS, INC., Davis, CA (US)

(72) Inventors: Ana Lucia Cordova-Kreylos, Davis, CA (US); Scott Burman, Davis, CA (US); Debora Wilk, Davis, CA (US)

(73) Assignee: MARRONE BIO INNOVATIONS, INC., Davis, CA (US)

( * ) Notice: Subject to any disclaimer, the term of this patent is extended or adjusted under 35 U.S.C. 154(b) by 57 days.

(21) Appl. No.: 16/410,398

(22) Filed: May 13, 2019

(65) Prior Publication Data

US 2019/0271003 A1 Sep. 5, 2019

Related U.S. Application Data

(63) Continuation of application No. 15/507,258, filed as application No. PCT/US2015/047649 on Aug. 31, 2015, now Pat. No. 10,337,025.

(60) Provisional application No. 62/046,672, filed on Sep. 5, 2014.

(51) Int. Cl.
| | |
|---|---|
| *C12N 15/82* | (2006.01) |
| *C12N 9/52* | (2006.01) |
| *A01N 63/10* | (2020.01) |
| *A01N 37/46* | (2006.01) |
| *A01N 37/18* | (2006.01) |
| *A01N 43/42* | (2006.01) |
| *C12N 15/10* | (2006.01) |
| *C12N 15/63* | (2006.01) |
| *A01N 37/00* | (2006.01) |
| *C12N 15/00* | (2006.01) |

(52) U.S. Cl.
CPC ......... *C12N 15/8286* (2013.01); *A01N 37/18* (2013.01); *A01N 37/46* (2013.01); *A01N 43/42* (2013.01); *A01N 63/10* (2020.01); *C12N 9/52* (2013.01); *C12N 15/10* (2013.01); *C12N 15/63* (2013.01); *C12N 15/82* (2013.01); *A01N 37/00* (2013.01); *C12N 15/00* (2013.01); *Y02A 40/146* (2018.01)

(58) Field of Classification Search
CPC .................................................. C12N 15/8286
See application file for complete search history.

(56) References Cited

U.S. PATENT DOCUMENTS

| 7,244,607 | B2 | 7/2007 | Martin et al. | |
|---|---|---|---|---|
| 9,187,531 | B2 | 11/2015 | Asolkar et al. | |
| 2007/0172463 | A1 | 7/2007 | Martin et al. | |
| 2011/0154536 | A1 | 6/2011 | Abad et al. | |
| 2012/0100236 | A1* | 4/2012 | Asolkar .................. | C12P 21/02 424/780 |

OTHER PUBLICATIONS

Martin et al., "Toxicity of Chromobacterium subtsugae to Southern Green Stink Bug (Heteroptera: *Pentatomidae*) and Corn Rootworm (Coleoptera: *Chrysomelidae*)"; Journal of Economic Entomology, Jun. 2007, vol. 100, No. 3, pp. 680-684.
Ciprandi, Alessandra et al., "Chromobacterium violaceum: importent insights for virulence and biotechnological potential by exoproteomic studies"; Current Microbiology, Pub. Feb. 28, 2013, vol. 57, No. 1, pp. 100-106.
International Search Report in PCT/US2015/047649 [KIPO] dated Nov. 23, 2015.
NCBI, GenBank accession No. AN78225.1 (Dec. 10, 2002).
Chinese Search Report (Translation) in 2015800474157 dated Apr. 29, 2020, pp. 1-3.

* cited by examiner

*Primary Examiner* — Weihua Fan
(74) *Attorney, Agent, or Firm* — Singleton Law, PLLC; Chainey P. Singleton; Ying-Horng Liu

(57) ABSTRACT

Disclosed herein are the nucleotide sequences of the *Chromobacterium subtsugae* genes. In addition, the amino acid sequences of proteins encoded by the *C. subtsugae* genes are provided. Nucleic acids, vectors and polypeptides comprising the aforementioned sequences are also provided. Homologues, functional fragments and conservative variants of the aforementioned sequences are also provided. Compositions having pesticidal, bioremedial and plant growth-promoting activities comprising *C. subtsugae* genes and proteins, and methods for the use of these compositions, are also provided.

6 Claims, No Drawings

Specification includes a Sequence Listing.

*CHROMOBACTERIUM SUBTSUGAE* GENES

CROSS-REFERENCE TO RELATED APPLICATIONS

This application is a Continuation application of U.S. patent application Ser. No. 15/507,258, filed Feb. 28, 2017, which is a National Stage of International Application Serial No. PCT/US2015/047649 filed on Aug. 31, 2015, and claims the priority of U.S. Provisional Application Ser. No. 62/046,672 filed on Sep. 5, 2014, the contents of which are incorporated in reference in their entirety.

INCORPORATION OF SEQUENCE LISTING

This instant application contains a Sequence Listing which has been submitted in ASCII format via EFS-Web and is hereby incorporated by reference in its entirety. Said ASCII copy is named MBI-203-0005-PCT_seq_ST25.txt and is 13,798 bytes in size.

TECHNICAL FIELD OF THE INVENTION

The present disclosure is in the field of biopesticides; in particular bacterial pesticides, their genes, gene products, and method of use thereof.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

*Chromobacterium subtsugae*

In 2000, a purple-pigmented bacterium (PRAA4-1) was isolated from forest soil in Maryland (Martin et al., 2004). In initial screens, this bacterium was found to be toxic to Colorado potato beetle and other insect pests (Martin et al., 2007a). Additional work with the isolate revealed activity gainst mites, grubs, diverse beetle species, aphids and plant parasitic nematodes, among other plant pests (Martin et al., 2007b, US Patent Application Publication No. 2012/0100236 A1). Some PRAA4-1 protein studies exist in the field of art with respect to protein actives against insects.

Proteases and Insect Control

Proteases have the ability to target and destroy essential proteins and tissues of insects. Plants have naturally evolved to express proteases to protect against insects. Insect predators also produce protease in their venom, which contributes to mortality. Proteases have been identified as important insecticidal agents for control of insects in agriculture.

Proteases with insecticidal activity fall into three general categories: cysteine proteases, metalloproteases and serine proteases. Proteases of these classes target the midgut, cuticle and hemocoel. The peritrophic matrix of the midgut is an ideal target for insect control because it lines and protects the midgut epithelium from food particles, digestive enzymes and pathogens; in addition to acting as a biochemical barrier (Hegedus at al., 2009). Enhancins are zinc metalloproteases expressed by baculoviruses that facilitate nucleopolyhedrovirus infections in lepidopterans (Lepore et al., 1996). These proteases promote the infection of lepidopteran larvae by digesting the invertebrate intestinal mucin protein of the peritrophic matrix, which in turn promotes infection of the midgut epithelium (Wang and Granados, 1997). Homologs of enhancin genes found in baculovirus have been identified in the genomes of *Yersinia pestis, Bacillus anthracis, Bacillus thuringiensis* and *Bacillus cereus* (Galloway et al., 2005; Hajaij-Ellouze et al., 2006).

Plant cysteine proteases also demonstrate activity against lepidopteran larvae. Cysteine proteases in the latex of the papaya and wild fig trees are essential in the defense against various lepidopteran larvae. Toxicity to the larvae was lost when the latex was washed or when the leaves were treated with a cysteine protease-inhibitor, indicating that the defense may be due to the high concentration of cysteine proteases in the latex (Konno et al., 2004).

Proteases that target the cuticle are also important in insect control. The cuticle covers the entire outside of the insect as well as some invaginations of internal structures. The cuticle is composed of a waxy epicuticle, an exocuticle and an endocuticle that consist of protein, lipid and chitin (Harrison and Bonning 2010). Fungal infection of insects by *Metarhizium anisopliae* and *Beauveria bassiana* occurs when the fungal spores germinate on the cuticle, forming structures for penetration of the cuticle by a variety of enzymes, including proteases (Freimoser at al., 2003; Cho et al., 2006). One notable serine protease produced by *M. anisopliae*, PR1A, digests the cuticle and plays an essential role in penetration (St. Leger et al. 1987). A clone of *M. anisopliae* was engineered to contain additional copies of the pr1a gene and showed 25% more kill of tobacco hornworm than the wild-type (St Leger et al., 1996). B. basianna was also engineered to express the *M. anisopliae* PR1A protease and demonstrated increased toxicity of larvae of the Masson's pine caterpillar, *Dendrolimus punctatus*, and the wax moth, *Galleria mellonella* (Lu et al., 2008).

The basement membrane of insects consists of proteins that surround the tissue and contribute to a variety of functions from structural support to barriers for viruses. Three potential basement membrane-degrading proteins were evaluated using *Autographa californica* multiple nucleopolyhedrovirus (AcMNPV). This baculovirus was engineered to express two vertebrate metalloproteases, rat stromelysin and human geatinase A, as well as the fruit fly cathepsin L, ScathL. The ScathL protease demonstrated the best baculovirus activity. The median survival time of infected tobacco budworm larvae was reduced by 50% when compared to wild-type infected larvae (Harrison and Bonning, 2001). This data supports the idea that proteases expressed in viruses have the ability to access the basement membrane of insects, which generally functions as a barrier to viruses. A previous report identified two basement membrane proteins of imaginal discs of fruit fly larvae that are susceptible to hydrolysis by cathepsin L (Homma and Natori, 1996). Purified ScathL protease was also toxic to a variety of insect pests when it was injected into the hemocoel. The purified protease demonstrated similar melanization, mortality and hemolymph protease activity in lepidopteran larvae as was seen ScathL expressed baculovirus infections (Li et al., 2008). Basement membrane damage is cause by purified ScathL protease both in vivo and in vitro (Tang et al., 2007; Philip et al. 2007).

Arthropod predators have also been shown to contain basement membrane cleaving proteases in their venom. One example is the parasitic wasp, *Eulophus pennicornis*, in which 3 metalloproteinases (EpMP1-3) were identified in the venom glands. Recombinant EpMP3 was injected into the hemocoel of *Lacanobia oleracea* larvae and resulted in significant mortality, or impaired development and growth in surviving larvae (Price et al., 2009). Social aphid soldier nymphs produce a toxic cathepsin B protease (cysteine protease) in their intestines. The protease is orally excreted into enemies and demonstrates insecticidal activity (Kutsukake et al., 2008).

A protease isolated from the bacterium, *Xenorhabdus nematophilia*, has been shown to suppress antibacterial peptides involved in insect immune response, making the insect susceptible to the pathogenetic process (Caldas et al., 2002). The enterobacterium, *Photorhabdus luminscense*, has been shown to be pathogenic to a broad spectrum of insects. The genome sequence of this bacterium identified genes related to toxicity, including proteases (Duchaud et al., 2003).

The use of proteases as insecticides has been of interest to plant modifications as well. Basement-membrane degrading proteases have been characterized and engineered for transgenic insecticidal protocols, with the goal of developing transgenic plants that are resistant to insect pests (U.S. Pat. No. 6,673,340, Harrison and Bonning, 2004). Proteases in the gut of insects have been shown to affect the impact of *Bacillus thuringiensis* Cry insecticidal proteins. Some proteases activate Cry proteins by processing them from a protoxin to a toxic form. Insect toxins have been modified to comprise proteolytic activation sites with the goal of incorporating this modification into transformed plants, plant cells and seeds. Cleavage of these sites by the insect gut protease results in an active insect toxin within the gut of the pest (U.S. Pat. No. 7,473,821, Abad et al., 2009).

Insecticidal Activity of Chitinases

Chitinases expedite insecticidal activity by puncturing the insect midgut lining and degrading the insect cuticle. Degradation of these membranes exposes the insects to pathogens, to other insecticidal compounds, and/or to plant defenses.

Chitinases hydrolyze the structural polysaccharide chitin, a linear homopolymer of 2-acetamido-2-deoxy-D-glucopyranoside, linked by β-1→4-linkages, which is a component of the exoskeleton and gut lining of insects. Chitinases are classified as either family 18 or family 19 glycosyl hydrolases. Family 18 chitinases are widespread, found in bacteria, plants, and animals; while family 19 chitinases are mainly found in plants (Henrissat and Bairoch, 1993). In insects, Chitinases play a role in molting (Samuels and Reynolds, 1993, Merzendorfer and Zimoch, 2003).

Chitinases alone show some insecticidal activity. Chitinase from Serretia marcenscens was found to be toxic to seventh instar *Galleria mellonella* larvae (Lysenk, 1976). Transgenic plants which express insect chitinases have been shown to have increased resistance to insect pestss. Tobacco plants were transformed with cDNA encoding a *Manduca sexta* chitinase. Leaves from these transgenic plants were infested with *Heliothis virescens* larvae. After 3 weeks it was found that chitinase positive leaves had less larval biomass and feeding damage than chitinase negative leaves. It is possible that the activity of the chitinases render insects more susceptible to plant defenses (Ding, et al., 1997).

Insect cuticles provide a physical barrier to protect the insect form pathogens or other environmental hazards, and are composed primarily of chitin (Kramer, et al., 1995). Entomopathogenic fungi *Metarhizium anisopliae, Beauvaria bassiana, Beauvaria amorpha, Verticillium lecanii*, and *Aspergillus flavus* all secrete chitinases to break down the cuticle and enter the insect host (St Leger, et al., 1986, 1992, Campos, et al. 2005). According to Kim, et al., chitinase-containing supernatants of *Beauveria bassina* were toxic to *Aphis gossypii* adults. However, when these supernatants were treated with an excess of chitin to inhibit the activity of the fungal chitinases, this mortality was significantly reduced, suggesting that chitinase plays an integral role in breaking down the cuticle and facilitating infection (Kim, et al. 2010). Chitinases have also been isolated from the venom of the endoparasitic wasp *Chelonus* sp., where they possibly help the venom penetrate the defenses of chitin protected prey (Krishnan, et al., 1994).

The peritrophic membrane, which lines the insect midgut, is another primarily-chitin-composed barrier that protects insects from pathogens. Any enzyme that can puncture this membrane has potential as a bioinsecticide (Wang and Granados, 2001). Hubner, et al. demonstrated that malarial parasites excrete chitinases to penetrate the peritrophic membrane in mosquitoes (Hubner, et al., 1991), and Shahabuddin, et al. confirmed that inhibition of chitinase with allosamidin is sufficient to prevent the malarial parasite *Plasmodium gallinaceum* from crossing the peritrophic membrane of *Anopheles freeborni*. Also, the addition of exogenous chitinase from *Streptomyces griseus* during the development of the *Anopheles freeborni* midgut prevented the formation of the peritrophic membrane (Shahabuddin, et al., 1993). This demonstrates that chitinases can break down the peritrophic membrane. Regev, et al. used *E. coli* to express *Serratia marcescens* endochitinase ChiA and confirmed with electron microscopy that *Spodoptera littoralis* larvae exposed to the endochitinase exhibited perforations in the peritrophic membrane (Regev, et al., 1996).

Because of the ability of chitinase to perforate the peritrophic membrane, endochitinases have also been shown to increase the insecticidal activity of *Bacillus thuringiensis* (Bt). *Choristoneura fumiferana* larvae reared on *Agies balsamea* treated with a mixture of a diluted commercial formulation of Bt and chitinase were killed more quickly than larvae reared on foliage treated with just Bt alone (Smirnoff, 1973). A mixture of a low concentration of Bt and *S. marcenscens* chitinase also resulted in higher mortality of *Spodoptera littoralis* larvae than Bt alone (Sheh et al., 1983). It is believed that this synergistic effect is due to puncturing of the peritrophic lining of the insect gut by the chitinase, facilitating the penetration of Bt spores into the insect. (Smirnoff, 1973).

Yen-Tc, an ABC type protein that is both necessary and sufficient for the entomopathogenicity of *Yersinia entomophaga* in the insect *Costelytra zealandica*, contains two family 18 chitinases, making it the first insecticidal toxin complex identified to incorporate chitinases. It is hypothesized that the chitinases are responsible for breaking down peritrophic membrane and exposing the midgut epithelial cells to the toxin. However, the chitinases may only be active in regions of the midgut with a relatively neutral pH (Busby, 2012).

Chitinases are also integral to the activity of some insect viruses. Hatwin, et al. created mutants of the *Autographa californica* nucleopolyhedrovirus (AcMNPV) that lacked the gene for chitinase. Usually, this virus causes liquefaction of the host larvae, facilitating the spread of the virus. This liquefaction did not occur when *Trichoplusia ni* larvae were infected with the chitinase negative virus. It was also confirmed that the AcMNPV chitinase is active under the alkaline conditions of the insect midgut (Hatwin, et al. 1997). A recombinant version of the same *Autographa californica* nucleopolyhedrovirus that expressed a *Haema*-

*physalis longicornis* chitinase was found to have bioarcaricidal activity against *Haemaphysalis longicornis* nymphs (Assegna, et al. 2006).

Rhs-Like Genes Encode Insecticidal Toxins

The rhs (rearrangement hotspot) gene family was first identified in *E. coli*. These genes confer chromosomal rearrangements by homologous exchange (Lin et al., 1984). They are 2 to 12 kb in size and exhibit a long core with a short tip. The core sequences are GC rich and highly conserved, but the tip sequences are GC-poor and highly variable. They encode proteins that have a large core domain and a short C-terminal tip domain. The protein core domain is hydrophilic and contains YD-repeats (Jackson et al., 2009). The Rhs proteins are capable of interacting with bacterial cell surfaces and binding to specific ligands (Wang et al., 1998). While the function of the Rhs proteins remains unknown (Hill et al., 1994), the structure is important because the YD repeats and highly conserved sequences resemble rhs and rhs-like genes encoding insecticidal toxins produced by bacteria.

*Photorhabdus luminescens* is a mutualistic symbiont of the nematodes from the Heterorhabditae family. The nematode infects the insect and injects the bacterium into the hemocoel of the insect. The bacterium then secretes toxins that kill the insect (Frost et al., 1997). Bowen et al. (1998), purified a high molecular weight protein associated with oral and injectable insecticidal toxicity that targets insects. In another study, Bowen et al. (1998) used high performance liquid chromatography to separate this protein into four toxin complexes (tc) termed, Tca, Tcb, Tcc, and Tcd encoded by the tc loci (Bowen et al., 1998). Waterfield et al. (2001) analyzed recombinant expression of the tc genes in *E. coli* to understand oral toxicity of Tc proteins. They found that without tccC-like homologs, they could not recover oral toxicity in *E. coli*. These authors concluded that TccC is involved in activation of toxin secretion. Furthermore, an amino acid sequence analysis revealed TccC and TccC-like proteins have a highly conserved core and highly variable extension. This structure bears resemblance to rhs-like elements (Waterfield N R, Bowen D J, Fetherston J D, Perry R D, and ffrench-Constant, R H, 2001). This similarity suggests that TccC-like and Rhs proteins share an ancient role in toxin mobility and activation for the Enterobacteriaceae family (ffrench-Constant, R et al, 2003).

Another microbe, *Serratia entomophila*, has insecticidal activity that targets New Zealand grass grub, *Costelytra zealandica*, and causes amber disease (Grimont et al., 1988). The virulence of *S. entomophila* is linked to a large plasmid called amber disease-associated plasmid (pADAP) (Glare et al., 1993). Hurst et al. analyzed the mutagenesis and the nucleotide sequence of pADAP to understand how it confers pathogenicity to grass grub. They found that pADAP encodes three genes responsible for the symptoms of amber disease, sepA, sepB, and sepC. All three genes are required for pathogenicity because a mutation in these genes abolishes amber disease. They illustrated that proteins encoded by the sep genes are similar to the proteins encoded by the insecticidal toxin complexes of *P. luminescens*. For example, the first 680 amino acids of SepC and TccC show a strong similarity. Furthermore, this region resembles the rhs elements of *E. coli*. The sepC gene is smaller than Rhs elements, but it encodes a hydrophilic protein core with nine Rhs peptide variants. Based on the similarity between the sep and tc genes, Hurst et al. concludes that these products are part of a new group of insecticidal toxins (Hurst et al., 2000).

Harada et al. discovered that, *Pantoea stewartii* ssp. DC283 is an aggressive pathogen that infects aphids (Harada et al., 1996). The aphid ingests the bacterium and DC283 is able to aggregate in the gut and cause death of the aphid. Stavrinides et al. performed a mutagenesis screen and discovered that the ucp1 (you c annot pass) locus is responsible for the virulence of DC283. Analysis of the ucp1 gene sequence revealed similarities to the Rhs protein family. ucp1 gene is smaller than the genes encoding RHS/YD proteins and does not have a ligand binding YD repeat, but it has conserved 5'-cores, non-homologous 3'ends, and it is a membrane bound protein. These structural similarities suggest enteric plant colonizers have the genetic ability to colonize insect hosts. Furthermore, the similarities between the ucp1 and rhs genes suggest that rhs-like genes have potential insecticidal activity (Stavrinides et al., 2010).

Despite these known protein, it is possible that insects may evolve resistance to plants expressing these known genes. Accordingly, there is a need to find novel proteins that have insecticidal activities.

SUMMARY OF THE INVENTION

In one aspect, the present disclosure provides the nucleotide sequence of insecticidal proteins from bacterium *Chromobacterium subtsugae*. Isolation and partial characterization of this bacterium is described, for example, in U.S. Pat. No. 7,244,607. Additionally provided are amino acid sequences of polypeptides encoded by the *Chromobacterium subtsugae* insecidal proteins.

In another aspect, the present disclosure provides isolated nucleic acids (e.g., DNA, RNA, nucleic acid analogues) comprising *C. subtsugae* insecidal proteins sequences, gene sequences, fragments thereof, and or mutant variants. Also provided are nucleic acid vectors (e.g., plasmid vectors, viral vectors), including expression vectors, comprising nucleic acids having *C. subtsugae* gene sequences, and/or fragments thereof. Exemplary bacterial vectors include, but are not limited to, *Agrobacterium tumefaciens, Rhizobium* sp. NGR234, *Sinorhizobium meliloti*, and *Mesorhizobium loti*.

Exemplary viral vectors include, but are not limited to, cauliflower mosaic virus (CaMV), pea early browning virus (PEBV), bean pod mottle virus (BPMV), cucumber mosaic virus (CMV), apple latent spherical virus (ALSV), tobacco mosaic virus (TMV), potato virus X, brome mosaic virus (BMV) and barley stripe mosaic virus (BSMV).

Cells transfected with the foregoing nucleic acids or vectors are also provided. Such cells can be plant cells, insect cells, mammalian cells, bacterial cells, or fungal cells (e.g., yeast). Plants comprising cells (plant or otherwise) that have been transfected with the foregoing nucleic acids or vectors, seeds from said plants, and the progeny of said plants are also provided. Transfected bacterial cells can include Agrobacteria (e.g., *Agrobacterium tumefaciens*), *Rhizobium, Sinorhizobium meliloti*, and *Mesorhizobium loti*. Insect vectors (e.g., *Homalodisca vitripennis*, the glassy-winged sharpshooter) comprising nucleic acid vectors which themselves comprise *C. subtsugae* sequences, are also provided.

In additional embodiments, polypeptides encoded by the *C. subtsugae* genes are provided. Functional fragments of *C. subtsugae* polypeptides, and conservatively substituted variants of *C. subtsugae* polypeptides, are also provided.

In further embodiments, plants comprising one or more isolated nucleic acids comprising *C. subtsugae* gene sequences and/or fragments thereof are provided. These isolated nucleic acids can be present on the exterior of the plant or internally within or between cells.

In additional embodiments, plants comprising one or more nucleic acid vectors, wherein said vector or vectors comprise *C. subtsugae* gene sequences and/or fragments thereof, are provided. Said vectors can be present on the exterior of the plant or internally.

In yet additional embodiments, plants comprising one or more *C. subtsugae* polypeptides are provided. Said *C. subtsugae* polypeptides can be present on the exterior of the plant or internally.

Also provided are plants comprising one or more functional fragments and/or one or more conservatively substituted variants of a *C. subtsugae* polypeptide or polypeptides. Said fragments and/or conservatively substituted variants can be present on the exterior of the plant or internally.

Progeny of the aforementioned plants are also provided. In addition, seeds from the aforementioned plants, and from their progeny, are provided.

Also disclosed herein are methods for controlling pests; e.g., methods for modulating pest infestation in a plant. Such pests can be, for example, insects, fungi, nematodes, mites, moths or aphids. The methods include application of a nucleic acid comprising a *C. subtsugae* gene sequence or fragment thereof to a plant, either internally or externally. Additional methods include application of a *C. subtsugae* polypeptide, or fragment thereof, or conservatively substituted variant thereof, to a plant, either internally or externally.

Also provided are pesticidal (e.g., insecticidal) compositions comprising nucleic acids and/or polypeptides encoded by the *C. subtsugae* genes. Such compositions can optionally include other insecticides or pesticides, either naturally-occurring or man-made.

Disclosed herein, inter alia, are the following embodiments:

1. A cell comprising a recombinant vector having a heterologous promoter operately linked to a nucleotide encoding a polypeptide with 95% identity to SEQ ID NOs: 1-3.

2. A plant or plant parts comprising one or more cells according to embodiment 1 or progeny or seed thereof.

3. The plant or plant parts of embodiment 2, wherein said plant part is selected from the group consisting of pollen, ovule, flower, shoot, root, stalk, silk, tassel, ear, and leaf tissue.

5. An antibody that binds to the polypeptide of embodiment 1.

6. The cell of embodiment 1, wherein said cell is a bacterial, mammalian, or fungal cell.

7. A method of producing an insect resistant plant comprising the step of transforming the recombinant vector of embodiment 1 into a plant cell.

8. Anti-counterfeit milled seed having, as an indication of origin, a plant cell of embodiment 1.

9. A pesticidal composition comprising (a) one or more nucleic acids and/or polypeptides having a sequence as set forth in SEQ ID NOS:1-6 and (b) a carrier.

10. The pesticidal composition of embodiment 9, wherein the composition is an insecticide.

11. The pesticidal composition of embodiment 10, further comprising a second pesticide.

12. The pesticidal composition of embodiment 11, wherein the second pesticide is an insecticide.

13. A method for modulating pest infestation in a plant, the method comprising contacting a plant or a plant part with an amount of the pesticidal composition according to embodiment 9 effective to modulate said pest infestation.

14. The method of embodiment 13, wherein the pest is selected from the group consisting of insects, fungi, nematodes, bacteria and mites.

15. The method of embodiment 14, wherein the insects comprise cabbage loopers, Beet armyworms, lygus, or Diamondback Moth.

16. A seed coating material comprising the polypeptide of embodiment 1, and one or more of a carrier, diluent, or adjuvant.

DETAILED DESCRIPTION OF THE INVENTION

Practice of the present disclosure employs, unless otherwise indicated, standard methods and conventional techniques in the fields of agriculture, plant molecular biology, entomology, cell biology, molecular biology, biochemistry, recombinant DNA and related fields as are within the skill of the art. Such techniques are described in the literature and thereby available to those of skill in the art. See, for example, Alberts, B. et al., "Molecular Biology of the Cell," 5 edition, Garland Science, New York, N.Y., 2008; Voet, D. et al. "Fundamentals of Biochemistry: Life at the Molecular Level," 3'd edition, John Wiley & Sons, Hoboken, N.J., 2008; Sambrook, J. et al., "Molecular Cloning: A Laboratory Manual," 3rd edition, Cold Spring Harbor Laboratory Press, 2001; Ausubel, F. et al., "Current Protocols in Molecular Biology," John Wiley & Sons, New York, 1987 and periodic updates; Glover, DNA Cloning: A Practical Approach, volumes I and II, IRL Press (1985), volume III, IRL Press (1987); Perbal, A Practical Guide to Molecular Cloning, John Wiley & Sons (1984); Rigby (ed.), The series "Genetic Engineering" (Academic Press); Setlow & Hollaender (eds.), The series "Genetic Engineering: Principles and Methods," Plenum Press; Gait (ed.), Oligonucleotide Synthesis: A Practical Approach, IRL Press (1984, 1985); Eckstein (ed.) Oligonucleotides and Analogues: A Practical Approach, IRL Press (1991); Hames & Higgins, Nucleic Acid Hybridization: A Practical Approach, IRL Press (1985); Hames & Higgins, Transcription and Translation: A Practical Approach, IRL Press (1984); B. Buchanan, W. Gruissem & R. Jones (eds.) "Biochemistry and Molecular Biology of Plants," Wiley (2002) and the series "Methods in Enzymology," Academic Press, San Diego, Calif. The disclosures of all of the foregoing references are incorporated by reference in their entireties for the purpose of describing methods and compositions in the relevant arts.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," and "the" include plural references unless the context clearly dictates otherwise.

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e., operably linked.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell.

Constructs may include any promoter or leader known in the art. For example, a promoter may be operably linked to a heterologous non-translated 5' leader such as one derived from a heat shock protein gene (see, for example, U.S. Pat. Nos. 5,659,122 and 5,362,865). Alternatively, a leader may be operably linked to a heterologous promoter such as the Cauliflower Mosaic Virus 35S transcript promoter (see, U.S. Pat. No. 5,352,605).

As used herein, the term "transcribable polynucleotide molecule" refers to any DNA molecule capable of being transcribed into a RNA molecule, including, but not limited to, those having protein coding sequences (SEQ ID NOs:4-6) and those having sequences useful for gene suppression. A "transgene" refers to a transcribable polynucleotide molecule heterologous to a host cell and/or a transcribable polynucleotide molecule artificially incorporated into a host cell's genome.

A promoter may be operably linked to a transcribable polynucleotide molecule that is heterologous with respect to the promoter molecule. As used herein, the term "heterologous" refers to the combination of two or more polynucleotide molecules when such a combination would not normally be found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of an RNA transcript is desired. Such expression of an RNA transcript may result in translation of the resulting mRNA molecule and thus protein expression. Alternatively, a transcribable polynucleotide molecule may be designed to ultimately cause decreased expression of a specific gene or protein that can enhance protein expression of SEQ ID NOs: 1-3. This may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complementary RNA molecule inside the cell. This duplex RNA molecule cannot be translated into a protein by the cell's translational machinery and is degraded in the cell. Any gene may be negatively regulated in this manner.

Polynucleotides and Oligonucleotides

A polynucleotide is a polymer of nucleotides, and the term is meant to embrace smaller polynucleotides (fragments) generated by fragmentation of larger polynucleotides. The terms polynucleotide and nucleic acid encompass both RNA and DNA, as well as single-stranded and double-stranded polynucleotides and nucleic acids. Polynucleotides also include modified polynucleotides and nucleic acids, containing such modifications of the base, sugar or phosphate groups as are known in the art.

An oligonucleotide is a short nucleic acid, generally DNA and generally single-stranded. Generally, an oligonucleotide will be shorter than 200 nucleotides, more particularly, shorter than 100 nucleotides, most particularly, 50 nucleotides or shorter.

Modified bases and base analogues, e.g., those able to form Hoogsteen and reverse Hoogsteen base pairs with the naturally-occurring bases, are known in the art. Examples include, but are not limited to, 8-oxo-adenosine, pseudoisocytidine, 5-methyl cytidine, inosine, 2-aminopurine and various pyrrolo- and pyrazolopyrimidine derivatives. Similarly, modified sugar residues or analogues, for example 2'-O-methylribose or peptide nucleic acid backbones, can also form a component of a modified base or base analogue. See, for example, Sun and Helene (1993) *Curr. Opin. Struct. Biol.* 3:345-356. Non-nucleotide macromolecules capable of any type of sequence-specific interaction with a polynucleotide are useful in the methods and compositions disclosed herein. Examples include, but are not limited to, peptide nucleic acids, minor groove-binding agents and antibiotics. New modified bases, base analogues, modified sugars, sugar analogues, modified phosphates and phosphate analogues capable of participating in duplex or triplex formation are available in the art, and are useful in the methods and compositions disclosed herein.

Homology and Identity of Nucleic Acids and Polypeptides

"Homology" or "identity" or "similarity" as used herein in the context of nucleic acids and polypeptides refers to the relationship between two polypeptides or two nucleic acid molecules based on an alignment of the amino acid sequences or nucleic acid sequences, respectively. Homology and identity can each be determined by comparing a position in each sequence which may be aligned for purposes of comparison. For example, a "reference sequence" can be compared with a "test sequence." When a position in the reference sequence is occupied by the same base or amino acid at an equivalent position in the test sequence, then the molecules are identical at that position; when the equivalent position is occupied by a similar amino acid residue (e.g., similar in steric and/or electronic nature), then the molecules can be referred to as homologous (similar) at that position. The relatedness of two sequences, when expressed as a percentage of homology/similarity or identity, is a function of the number of identical or similar amino acids at positions shared by the sequences being compared. In comparing two sequences, the absence of residues (amino acids or nucleic acids) or presence of extra residues, in one sequence as compared to the other, also decreases the identity and homology/similarity.

As used herein, the term "identity" refers to the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the highest degree of match between the sequences tested. Moreover, methods to determine identity are codified in publicly available computer programs. Computer program methods to determine identity between two sequences include, but are not limited to, the GCG program package (Devereux et al. (1984) *Nucleic Acids Research* 12:387), BLASTP, BLASTN, and FASTA (Altschul et al. (1990) *J. Molec. Biol.* 215:403-410; Altschul et al. (1997) *Nucleic Acids Res.* 25:3389-3402). The BLAST X program is publicly available from NCBI and other sources. See, e.g., *BLAST Manual*, Altschul, S., et al., NCBI NLM NIH Bethesda, Md. 20894; Altschul et al. (1990) *J. Mol. Biol.* 215:403-410. The well known Smith-Waterman algorithm can also be used to determine identity.

For sequence comparison, typically one sequence acts as a reference sequence, to which one or more test sequences are compared. Sequences are generally aligned for maximum correspondence over a designated region, e.g., a region at least about 20, 25, 30, 35, 40, 45, 50, 55, 60, 65 or more amino acids or nucleotides in length, and the region can be as long as the full-length of the reference amino acid sequence or reference nucleotide sequence. When using a sequence comparison algorithm, test and reference sequences are input into a computer program, subsequence coordinates are designated, if necessary, and sequence algorithm program parameters are designated. The sequence comparison algorithm then calculates the percent sequence identity for the test sequence(s) relative to the reference sequence, based on the designated program parameters.

Examples of algorithms that are suitable for determining percent sequence identity are the BLAST and BLAST 2.0 algorithms, which are described in Altschul et al. (1990) *J. Mol. Biol.* 215:403-410 and Altschul et al. (1977) *Nucleic Acids Res.* 25:3389-3402, respectively. Software for performing BLAST analyses is publicly available through the National Center for Biotechnology Information at www.ncbi.nlm.nih.gov. Further exemplary algorithms include ClustalW (Higgins et al. (1994) *Nucleic Acids Res.* 22:4673-4680), available at www.ebi.ac.uk/Tools/clustalw/index.html.

In another embodiment, sequence identity between two nucleic acids can also be described in terms of annealing, reassociation, or hybridization of two polynucleotides to each other, mediated by base-pairing. Hybridization between polynucleotides proceeds according to known and art-recognized base-pairing properties, such that adenine base-pairs with thymine or uracil, and guanine base-pairs with cytosine. The property of a nucleotide that allows it to base-pair with a second nucleotide is called complementarity. Thus, adenine is complementary to both thymine and uracil, and vice versa; similarly, guanine is complementary to cytosine and vice versa. An oligonucleotide or polynucleotide which is complementary along its entire length with a target sequence is said to be perfectly complementary, perfectly matched, or fully complementary to the target sequence, and vice versa. Two polynucleotides can have related sequences, wherein the majority of bases in the two sequences are complementary, but one or more bases are noncomplementary, or mismatched. In such a case, the sequences can be said to be substantially complementary to one another. If two polynucleotide sequences are such that they are complementary at all nucleotide positions except one, the sequences have a single nucleotide mismatch with respect to each other.

The term "substantially identical" refers to identity between a first amino acid sequence that contains a sufficient or minimum number of amino acid residues that are i) identical to, or ii) conservative substitutions of, aligned amino acid residues in a second amino acid sequence such that the first and second amino acid sequences share a common structural domain and/or common functional activity. For example, amino acid sequences that contain a common structural domain having at least about 90%, 91%, 92%, 93%, 94%, 95%, 96%, 97%, 98%, 99% or 99.5% identity to an amino acid sequence as disclosed herein (i.e., SEQ ID NOs:1-3) are termed substantially identical. In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional or structural activity, or encode a common structural polypeptide domain or a common functional polypeptide activity.

In another embodiment, the term "homology" describes a mathematically based comparison of sequence similarities which is used to identify genes or proteins with similar functions or motifs. A reference nucleotide or amino acid sequence (e.g., a sequence as disclosed herein) is used as a "query sequence" to perform a search against public databases to, for example, identify other family members, related sequences or homologues. Such searches can be performed using the NBLAST and XBLAST programs (version 2.0) of Altschul et al. (1990) *J. Mol. Biol.* 215:403-410. BLAST nucleotide searches can be performed with the NBLAST program, score=100, wordlength=12 to obtain nucleotide sequences homologous to a reference nucleotide sequence. BLAST amino acid searches can be performed with the XBLAST program, score=50, wordlength=3 to obtain amino acid sequences homologous to a reference amino acid sequence. To obtain gapped alignments for comparison purposes, Gapped BLAST can be utilized as described in Altschul et al. (1997) Nucleic Acids Res. 25:3389-3402. When utilizing the BLAST and Gapped BLAST programs, the default parameters of the respective programs (e.g., XBLAST and BLAST) can be used (see the world wide web at: ncbi.nlm.nih.gov).

Nucleic acids and polynucleotides of the present disclosure encompass those having an nucleotide sequence that is at least 75%, at least 80%, at least 90%, at least 95%, at least 98%, at least 99%, at least 99.5% or 100% identical to any of SEQ ID NOs:4-6.

Nucleotide analogues and amino acid analogues are known in the art. Accordingly, nucleic acids (i.e., SEQ ID NOs:4-6) comprising nucleotide analogues and polypeptides (i.e., SEQ ID NOs:1-3) comprising amino acid analogues are also encompassed by the present disclosure.

Transcribable polynucleotide molecules can be genes of agronomic interest. As used herein, the term "gene of agronomic interest" refers to a transcribable polynucleotide molecule that when expressed in a particular plant tissue, cell, or cell type provides a desirable characteristic associated with plant morphology, physiology, growth, development, yield, product, nutritional profile, disease or insect/pest resistance, and/or environmental or chemical tolerance. Genes of agronomic interest include, but are not limited to, insect control genes encoded by SEQ ID NOs: 4-6 or its associated protein SEQ ID NOs:1-3, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression to enhance protein expressions of SEQ ID NO: 1-3. The product of a gene of agronomic interest can act within the plant in order to cause an effect upon the plant physiology or metabolism or can be act as a pesticidal agent in the diet of a pest that feeds on the plant.

As used herein, "control plant" means a plant that does not contain the recombinant DNA that expressed a protein which imparts an enhanced trait. A control plant is to identify and select a plant that has an enhance trait. A suitable control plant can be a non-transgenic plant of the parental line used to generate a transgenic plant, e.g., devoid of recombinant DNA. A suitable control plant can in some cases be a progeny of a hemizygous transgenic plant line that is does not contain the recombinant DNA, known as a negative segregant.

As used herein, an "enhanced trait" means a characteristic of a transgenic plant that includes, but is not limited to, an enhance agronomic trait characterized by enhanced insect resistance, enhanced plant morphology, physiology, growth and development, yield, nutritional enhancement, disease or pest resistance, or environmental or chemical tolerance. In more specific aspects of this invention enhanced trait is selected from group of enhanced traits consisting of enhanced water use efficiency, enhanced cold tolerance, increased yield, enhanced nitrogen use efficiency, enhanced seed protein and enhanced seed oil. In an aspect of the invention the enhanced trait is enhanced yield including increased yield under non-stress conditions and increased yield under environmental stress conditions. Stress conditions can include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a plant can be measured in a number of ways, including test weight, seed number per plant, seed weight, seed number per unit area (e.g., seeds, or weight of seeds, per acre), bushels per acre, tonnes per acre, tons per acre, kilo per hectare. For example, maize yield can be measured as production of shelled corn kernels per unit of production area in bushels per acre or metric tons per hectare, often reported on a moisture adjusted basis at about 15.5 percent moisture. Increased yield can result from improved utilization of key biochemical compounds such as nitrogen, phosphorous and carbohydrate, or from improved responses to environmental stresses, such as cold, heat, drought, salt, and attack by pests or pathogens.

Conservative Substitutions and Functional Fragments

In comparing amino acid sequences, residue positions which are not identical can differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. With respect to a reference polypeptide sequence, a test polypeptide sequence that differs only by conservative substitutions is denoted a "conservatively substituted variant" of the reference sequence.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are known in the art. Similarly, methods for determining protein function are known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, either genetic and biochemical. See, for example, Fields et al. (1989) Nature 340:245 246; U.S. Pat. No. 5,585,245 and PCT WO 98/44350.

Typically, a functional fragment retains at least 50% of the activity or function of the polypeptide. In some embodiments, a functional fragment retains at least 55%, at least 60%, at least 65%, at least 70%, at least 75%, at least 80%, at least 85%, at least 90%, at least 95%, at least 99% or 100% of the activity or function of the polypeptide.

A functional fragment of a polypeptide can include conservative amino acid substitutions (with respect to the native polypeptide sequence) that do not substantially alter the activity or function of the polypeptide. The term "conservative amino acid substitution" refers to grouping of amino acids on the basis of certain common structures and/or properties. With respect to common structures, amino acids can be grouped into those with non-polar side chains (glycine, alanine, valine, leucine, isoleucine, methionine, proline, phenylalanine and tryptophan), those with uncharged polar side chains (serine, threonine, asparagine, glutamine, tyrosine and cysteine) and those with charged polar side chains (lysine, arginine, aspartic acid, glutamic acid and histidine). A group of amino acids containing aromatic side chains includes phenylalanine, tryptophan and tyrosine. Heterocyclic side chains are present in proline, tryptophan and histidine. Within the group of amino acids containing non-polar side chains, those with short hydrocarbon side chains (glycine, alanine, valine, leucine, isoleucine) can be distinguished from those with longer, non-hydrocarbon side chains (methionine, proline, phenylalanine, tryptophan). Within the group of amino acids with charged polar side chains, the acidic amino acids (aspartic acid, glutamic acid) can be distinguished from those with basic side chains (lysine, arginine and histidine).

A functional method for defining common properties of individual amino acids is to analyze the normalized frequencies of amino acid changes between corresponding proteins of homologous organisms (Schulz, G. E. and R. H. Schirmer, Principles of Protein Structure, Springer-Verlag, 1979). According to such analyses, groups of amino acids can be defined in which amino acids within a group are preferentially substituted for one another in homologous proteins, and therefore have similar impact on overall protein structure (Schulz, G. E. and R. H. Schirmer, supra). According to this type of analysis, conservative amino acid substitution" refers to a substitution of one amino acid residue for another sharing chemical and physical properties of the amino acid side chain (e.g., charge, size, hydrophobicity/hydrophilicity). Following are examples of amino acid residues sharing certain chemical and/or physical properties:

(i) amino acids containing a charged group, consisting of Glu, Asp, Lys, Arg and His, (ii) amino acids containing a positively-charged group, consisting of Lys, Arg and His, (iii) amino acids containing a negatively-charged group, consisting of Glu and Asp, (iv) amino acids containing an aromatic group, consisting of Phe, Tyr and Trp, (v) amino acids containing a nitrogen ring group, consisting of His and Trp, (vi) amino acids containing a large aliphatic non-polar group, consisting of Val, Leu and Ile, (vii) amino acids containing a slightly-polar group, consisting of Met and Cys, (viii) amino acids containing a small-residue group, consisting of Ser, Thr, Asp, Asn, Gly, Ala, Glu, Gln and Pro, (ix) amino acids containing an aliphatic group consisting of Val, Leu, Ile, Met and Cys, and (x) amino acids containing a hydroxyl group consisting of Ser and Thr.

Certain "conservative substitutions" may include substitution within the following groups of amino acid residues: gly, ala; val, ile, leu; asp, glu; asn, gln; ser, thr; lys, arg; and phe, tyr.

Thus, as exemplified above, conservative substitutions of amino acids are known to those of skill in this art and can be made generally without altering the biological activity or function of the resulting molecule. Those of skill in this art also recognize that, in general, single amino acid substitutions in non-essential regions of a polypeptide do not substantially alter biological activity. See, e.g., Watson, et al., "Molecular Biology of the Gene," 4th Edition, 1987, The Benjamin/Cummings Pub. Co., Menlo Park, Calif., p. 224.

Polypeptides of the present disclosure encompass those having 1, 2, 3, 4, 5, 6, 7, 8, 9 or 10 or more amino acid substitutions compared to an amino acid sequence as set forth in SEQ ID NOs:1-3, e.g., conservative amino acid substitutions. Amino acid residues that can be substituted can be located at residue positions that are not highly conserved. The ordinarily skilled artisan will appreciate that, based on location of the active sites and/or on homology to related proteins, a protein will tolerate substitutions, deletions, and/or insertions at certain of its amino acid residues, without significant change in its overall physical and chemical properties.

Polypeptides of the present disclosure encompass those having an amino acid sequence that is at least 75%, at least 80%, at least 90%, at least 95%, at least 96%, at least 97%, at least 98%, at least 99%, at least 99.5%, or 100% identical to any of the polypeptides shown in SEQ ID NOs:1-3.

RNA Suppression

Small RNAs that regulate protein expression include miRNAs and ta-siRNAs. A miRNA is a small (typically about 21 nucleotide) RNA that has the ability to modulate the expression of a target gene by binding to messenger RNA for the target protein leading to destabilization of the target protein messenger RNA or translational inhibition of the target protein messenger RNA, ultimately resulting in reduction of the target protein. The design and construction of ta-siRNA constructs and their use in the modulation of protein in transgenic plant cells is disclosed by Allen and Carrington in US Patent Application Publication US 2006/0174380 A1 which is incorporated herein by reference. The expression or suppression of such small RNAs are aspects of the invention that are conveniently illustrated by reference to use of miRNAs.

Recombinant DNA constructs can be used to modify the activity of native miRNAs by a variety of means. By increasing the expression of a miRNA, e.g. temporally or spatially, the modulation of expression of a native target gene can be enhanced. An alternative gene suppression approach for suppressing the expression of a target protein can include the use of a recombinant DNA construct that produces a synthetic miRNA that is designed to bind to a native or synthetic miRNA recognition site on messenger RNA for the target protein.

By reducing the expression of a miRNA, the modulation of a native target gene can be diminished resulting in enhanced expression of the target protein, such as SEQ ID NOs: 1-3. More specifically, the expression of a target protein can be enhanced by suppression of the activity of the miRNA that binds to a recognition site in the messenger RNA that is transcribed from the native gene for the target protein. Several types of recombinant DNA constructs can be designed to suppress the activity of a miRNA.

For example, a recombinant DNA construct that produces an abundance of RNA with the miRNA recognition site can be used as a decoy for the native miRNA allowing endogenous messenger RNA with the miRNA recognition site to be translated to the target protein without interference from native miRNA. A recombinant DNA construct that produces RNA with a modified miRNA recognition site, e.g. with nucleotides at positions 10 and/or 11 in a 21 mer miRNA recognition site which are unpaired with respect to the native miRNA, can be used to sequester natively expressed miRNA thereby reducing the cleavage that normally occurs when miRNA binds to a recognition site. The unpaired nucleotides can be produced e.g. through additional nucleotides between positions 10 and 11 or through substitutions of the nucleotides at positions 10 and 11.

Additionally, a recombinant DNA construct can be created that produces RNA that can be processed in plants into synthetic small RNA (miRNA-like) that can bind endogenous miRNA recognition sites but is unable to induce cleavage of mRNA because the small RNA is modified, for instance by having a modified nucleotide at positions 10 and/or 11 or a deletion that produces a bulge between positions 10 and 11 when the small RNA is paired with the miRNA recognition site. The resulting synthetic small RNA, a cleavage blocker, can reduce endogenous miRNA binding and thus block cleavage of a protected miRNA target site enhancing the expression of a target protein.

A recombinant DNA construct designed for producing a modified messenger RNA for the protein where the native miRNA recognition site is modified to be resistant to the binding of cognate miRNA which regulates the native gene can also be used to express protein from heterologous messenger RNA that is no longer modulated by the native miRNA.

The activity of a miRNA which down-regulates an endogenous protein is enhanced by enhancing the expression of the miRNA or by enhancing the ability of the miRNA to bind an RNA encoding the target protein. A recombinant DNA encoding an RNA encoding the miRNA or a miRNA-sensitive messenger RNA encoding the protein in which a miRNA binding site is added are designed to enhance miRNA activity resulting in enhanced suppression of the target mRNA and cognate protein. Recombinant DNA encoding an RNA encoding a miRNA, or a miRNA-sensitive RNA are designed using methods disclosed in US Patent Application Publication US 2009/0070898 A1.

Some, if not many, miRNAs modulate the expression of multiple proteins or biochemical pathways. plants can be provided with enhanced traits not so much from the suppression or enhancement of the expression of a particular protein, as from change of enzyme activity in a pathway by modulating the level of a miRNA. Thus, aspects of this invention are achieved by enhanced miRNA activity resulting from use in plant cells of recombinant DNA constructs that produce an enhanced level of a miRNA. Other aspects of this invention are achieved by reduced miRNA activity resulting from use in transgenic plant cells of recombinant DNA constructs that produce a reduced level or activity of a miRNA.

*C. subtsugae* Nucleic Acids

Also provided are nucleotide sequences encoding *C. subtsugae* genes and nucleotide sequences of functional RNA molecules (e.g., rRNAs, tRNAs) (SEQ ID NOs:4-6). Nucleic acids comprising these sequences are also provided. Fragments of *C. subtsugae* gene sequences are also provided. Such fragments are 10 or more, 25 or more, 50 or more, 75 or more, 100 or more 200 or more, 500 or more, or 1,000 or more nucleotides in length. Nucleic acids having a sequence that is 50%, 55%, 60%, 65%, 70%, 75%, 80%, 85%, 90%, 95%, 96%, 97%, 98%, 99% or 99.9% identical to the aforementioned sequences are also provided. The nucleic acids disclosed herein can be either DNA or RNA, and can be either single-stranded or double-stranded. Nucleic acids comprising nucleotide sequences that are complementary to the aforementioned sequences are also provided, as are nucleic acids that hybridize to the aforementioned nucleic acids under stringent conditions.

The present disclosure also provides polynucleotides comprising a nucleotide sequence encoding any of the polypeptide sequences disclosed herein. Such a polynucleotide has a nucleotide sequence that is at least 70% (e.g., at least 75%, at least 80%, at least 85%, at least 90%, at least 95%, at least 98%, at least 99%, at least 99.5% or 100%) identical to a contiguous sequence of a nucleic acid that encodes any of the polypeptides disclosed herein. The percentage identity is based on the shorter of the sequences compared. Known programs such as BLASTN (2.0.8) (Altschul et al. (1997) *Nucl. Acids. Res.* 25:3389-3402) using default parameters and no filter can be employed to make a sequence comparison. Nucleic acid sequence identity (e.g. between two different polynucleotides encoding identical amino acid sequences) can be lower than the percent of amino acid sequence identity due to degeneracy of the genetic code.

Examples of nucleic acid sequences in a polynucleotide encoding a polypeptide of the present disclosure can be found among SEQ ID NOs:4-6. These nucleic acid sequences can also be provided in an expression vector (see below).

*C. subtsugae* Polypeptides and Proteins

The present disclosure provides the amino acid sequences of proteins encoded by the *C. subtsugae* genome, as well as polypeptides comprising said amino acid sequences (i.e., SEQ ID NOs:1-3). Functional fragments and conservatively-substituted variants of said polypeptides are also provided. In addition, fragments of the polypeptides disclosed herein that do not retain function are also provided and are useful, e.g., as epitopes for production of antibodies. Such fragments are 4 or more, 10 or more, 25 or more, 50 or more, 75 or more, 100 or more 200 or more, 500 or more, or 1,000 or more amino acids in length.

The present disclosure also provides a polypeptide comprising an amino acid sequence that is at least 50%, 55%, 60%, 65%, 70%, 75%, 80%, 85%, 90%, 95%, 96%, 97%, 98%, 98.5%, 99%, 99.5% or 99.9% identical to a contiguous sequence of a polypeptide as disclosed herein. The percentage identity is based on the shorter of the sequences compared. Methods for determining degree of polypeptide sequence identity are known in the art.

The subject polypeptides can include amino acid sequences derived from any of SEQ ID NOs:1-3 further comprising heterologous amino acid sequences. Such polypeptides can be fusion proteins, such as a fusion protein containing epitope tags, purification tags, and/or detectable labels. A fusion protein can optionally include a linker sequence between the heterologous sequences and the *C. subtsugae* amino acid sequence. Methods for producing fusion proteins are known in the art. Other heterologous elements and exemplary fusion proteins are described in more detail below.

Exemplary polypeptides containing heterologous elements may include myc and/or His6 tags and may optionally include flanking linker sequences.

Polypeptides of the present disclosure further encompass those that are joined to a reporter polypeptide, e.g., a fluorescent protein, and/or conjugated to a molecule. The molecule conjugated to the polypeptide can be a carrier molecule or a moiety that facilitates delivery and/or increases the half-life of the subject polypeptide.

Polypeptides of the present disclosure can be produced by any suitable method, including recombinant and non-recombinant methods (e.g., chemical synthesis). The subject polypeptide can be prepared by solid-phase synthesis methods known in the art, (e.g., Fmoc- or t-Boc chemistry), such as those described by Merrifield (1963) J. Am. Chem. Soc. 85:2149 and Methods in Molecular Biology, Vol 35: Peptide Synthesis Protocols.

It should be noted that the polypeptides of the present disclosure can also contain additional elements, such as a detectable label, e.g., a radioactive label, a fluorescent label, a biotin label, an immunologically detectable label (e.g., a hemagglutinin (HA) tag, a poly-Histidine tag) and the like. Additional elements can be provided (e.g., in the form of fusion polypeptides) to facilitate expression (e.g. N-terminal methionine and/or a heterologous signal sequence to facilitate expression in host cells), and/or isolation (e.g., biotin tag, immunologically detectable tag) of the polypeptides of the disclosure through various methods.

The polypeptides can also optionally be immobilized on a support through covalent or non-covalent attachment.

Isolation and purification of the subject polypeptides can be accomplished according to methods known in the art. The term "isolated" is intended to mean that a compound (e.g. polypeptide or polynucleotide) is separated from all or some of the components that accompany it in nature. "Isolated" also refers to the state of a compound separated from all or some of the components that accompany it during manufacture (e.g., chemical synthesis, recombinant expression, culture medium, and the like).

For example, a polypeptide according to the present disclosure can be isolated from a lysate of cells that have been genetically modified to express the subject polypeptide, from a cell culture medium, or from a synthetic reaction mixture. Isolation can additionally be achieved by immunoaffinity purification, which generally involves contacting a sample with an antibody (optionally immobilized) that specifically binds to an epitope of the polypeptide, washing to remove non-specifically bound material, and eluting specifically bound polypeptide. Isolated polypeptide can be further purified by dialysis and other methods normally employed in protein purification, e.g. metal chelate chromatography, ion-exchange, and size exclusion.

Homologues

In yet another embodiment, the present disclosure provides methods of obtaining homologues of the fragments of the *C. subtsugae* genes disclosed herein, and homologues of the proteins encoded by the ORFs disclosed herein. Specifically, by using the nucleotide and amino acid sequences disclosed herein as a probe or as primers, and techniques such as PCR cloning and colony/plaque hybridization, one skilled in the art can obtain said homologues. Such homologues can be obtained from any organism; e.g., other species of *Chromobacterium* or other bacteria.

In another embodiment, homologs can be identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. Because a protein hit with the best E-value for a particular organism may not necessarily be an ortholog, e.g., have the same function, or be the only ortholog, a reciprocal query is used to filter hit sequences with significant E-values for ortholog identification. The reciprocal query entails search of the significant hits against a database of amino acid sequences from the base organism that are similar to the sequence of the query protein. A hit can be identified as an ortholog, when the reciprocal query's best hit is the query protein itself or a protein encoded by a duplicated gene after speciation. A further aspect of the homologs encoded by DNA useful in the transgenic plants of the invention are those proteins that differ from a disclosed protein as the result of deletion or insertion of one or more amino acids in a native sequence.

Antibodies, Detection Methods, Kits

Also provided are antibodies which selectively bind a protein or polypeptide fragment encoded by the *C. subtsugae* genes such as SEQ ID NOs:1-3. Such antibodies, in addition, can comprise a detectable label and/or be attached to a solid support. Such antibodies include both monoclonal and polyclonal antibodies. Also provided are hybridomas which produce the above-described monoclonal antibodies.

In additional embodiments, the present disclosure provides methods of identifying test samples derived from cells that express one or more of the ORFs disclosed herein, or homologues thereof. Such methods comprise incubating a test sample with one or more of the antibodies of the present disclosure, or one or more fragments of the *C. subtsugae* genes, under conditions which allow a skilled artisan to determine if the sample contains the ORF (or portion thereof) or product produced therefrom.

In additional embodiments, kits are provided which contain the necessary reagents to carry out the above-described assays. Specifically, provided herein is a compartmentalized kit designed to receive, in close confinement, one or more containers which comprises: (a) a first container comprising one of the antibodies, or one of the *C. subtsugae* gene fragments of the present disclosure; and (b) one or more other containers comprising one or more of the following: wash reagents, reagents capable of detecting presence of bound antibodies or reagents capable of detecting presence of hybridized nucleic acids.

Using the isolated proteins disclosed herein, the present disclosure further provides methods of obtaining and identifying agents capable of binding to a protein encoded by a *C. subtsugae* ORF. Specifically, such agents include antibodies (described above), peptides, carbohydrates, pharmaceutical agents and the like. Such methods comprise the steps of: (a) contacting an agent with an isolated protein encoded by one of the ORFs disclosed herein; and (b) determining whether the agent binds to said protein. Methods for detecting protein-protein binding are known in the art and include, for example, filter-binding, immunoprecipitation, two-hybrid assays, gel retardation and reporter subunit complementation. See, for example, U.S. Pat. Nos. 5,503,977 and 5,585,245; Fields et al. (1989) Nature 340: 245-247; Bai et al. (1996) Meth. Enzymol. 273:331-347 and Luo et al. (1997) BioTechniques 22:350-352.

Vectors

For embodiments in which a polypeptide is produced using recombinant techniques, the methods can involve any suitable construct and any suitable host cell, which can be a prokaryotic or eukaryotic cell (e.g. a bacterial host cell, a yeast host cell, a plant host cell, an insect host cell, or a cultured mammalian host cell). Methods for introducing genetic material into host cells are known in the art and include, for example, biolistics, transformation, electroporation, lipofection, conjugation, calcium phosphate co-precipitation and the like. The method for transfer can be selected so as to provide for stable expression of the introduced polypeptide-encoding nucleic acid. The polypeptide-encoding nucleic acid can be provided as an inheritable episomal element (e.g., plasmid) or can be genomically integrated.

Viral vectors can also be used for cloning and expression of the nucleic acids disclosed herein. Exemplary plant viral vectors include cauliflower mosaic virus (CaMV), pea early browning virus (PEBV), bean pod mottle virus (BPMV), cucumber mosaic virus (CMV), apple latent spherical virus (ALSV), tobacco mosaic virus (TMV), potato virus X, brome mosaic virus (BMV) and barley stripe mosaic virus (BSMV).

Additional vectors can be used for expression of *C. subtsugae* polypeptide sequences in non-plant organisms. These include prokaryotic cloning vectors (e.g., pBR322, pUC, bacteriophage lambda), fungal vectors (e.g., yeast 2-micron plasmid), insect cloning vectors (e.g., baculovirus) and mammalian vectors (e.g., SV40).

Suitable vectors for transferring a polypeptide-encoding nucleic acid can vary in composition. Integrative vectors can be conditionally replicative or suicide plasmids, bacteriophages, and the like. The constructs can include various elements, including for example, promoters, selectable genetic markers (e.g., genes conferring resistance to antibiotics, for example, instance neomycin, G418, methotrexate, ampicillin kanamycin, erythromycin, chloramphenicol, or gentamycin), origins of replication (to promote replication in a host cell, e.g., a bacterial host cell), and the like. The choice of vector depends upon a variety of factors such as the type of cell in which propagation is desired and the purpose of propagation. Certain vectors are useful for amplifying and making large amounts of the desired DNA sequence. Other vectors are suitable for expression of protein in cells. Still other vectors are suitable for transfer and expression in cells in a whole animal or plant. The choice of appropriate vector is well within the skill of the art. Many such vectors are available commercially.

The vector used can be an expression vector based on episomal plasmids containing selectable drug resistance markers and elements that provide for autonomous replication in different host cells. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding the subject polypeptide, may provide for propagating the subject nucleic acids, or both.

Constructs can be prepared by, for example, inserting a polynucleotide of interest into a construct backbone, typically by means of DNA ligase attachment to a cleaved restriction enzyme site in the vector. Alternatively, the desired nucleotide sequence can be inserted by homologous recombination or site-specific recombination, or by one or more amplification methods (e.g., PCR). Typically homologous recombination is accomplished by attaching regions of homology to the vector on the flanks of the desired nucleotide sequence, while site-specific recombination can be accomplished through use of sequences that facilitate site-specific recombination (e.g., cre-lox, att sites, etc.). Nucleic acid containing such sequences can be added by, for example, ligation of oligonucleotides, or by polymerase chain reaction using primers comprising both the region of homology and a portion of the desired nucleotide sequence.

For expression of the polypeptide of interest, an expression cassette can be employed. Thus, the present disclosure provides a recombinant expression vector comprising a subject nucleic acid. The expression vector can provide transcriptional and translational regulatory sequences, and can also provide for inducible or constitutive expression, wherein the coding region is operably placed under the transcriptional control of a transcriptional initiation region (e.g., a promoter, enhancer), and transcriptional and translational termination regions. These control regions may be native to the *C. subtsugae* genome, or can be derived from exogenous sources. As such, control regions from exogenous sources can be considered heterologous elements that are operably linked to the nucleic acid encoding the subject polypeptide. In general, the transcriptional and translational regulatory sequences can include, but are not limited to, promoter sequences, operator sequences, ribosomal binding sites, transcriptional start and stop sequences, translational start and stop sequences, polyadenylation sites and enhancer or activator sequences. Promoters can be either constitutive or inducible, and can be a strong constitutive promoter (e.g., T7 promoter, SP6 promoter, and the like).

Exemplary plant regulatory sequences, which can be used in the recombinant constructs disclosed herein, include constitutive promoters such as the CaMV 19S and 35S promoters and those from genes encoding actin or ubiquitin. Alternatively, regulated promoters such as chemically-regulated promoters (e.g., tetracycline-regulated) and wound-inducible promoters (expressed at wound sites and at sites of phytopathogenic infection) can also be used. In additional embodiments, promoters can be tissue-specific (e.g., specifying expression in roots, leaves, flowers, inflorescences) and/or temporally regulated (e.g., specifying expression in seedlings).

Additional promoters for use in plant cells have been described. See, for example, Stanford et al. (1989) Mol. Gen. Genet. 215: 200-208; Xu et al. (1993) Plant Molec. Biol. 22: 573-588; Logemann et al. (1989) Plant Cell 1: 151-158; Rohrmeier & Lehle (1993) Plant Molec. Biol. 22: 783-792; Firek et al. (1993) Plant Molec. Biol. 22: 129-142 and Warner et al. (1993) Plant J. 3: 191-201.

Consensus plant translation initiation sequences (i.e., ribosome-binding sites) have been described by Joshi (1987) Nucleic Acids Res. 15:6643-6653 and in the Clontech Catalogue 1993/1994, page 210.

Expression vectors generally have convenient restriction sites located near the promoter sequence to provide for the insertion of nucleic acid sequences encoding proteins of interest. A selectable marker operative in the expression host can be present to facilitate selection of cells containing the vector. In addition, the expression construct can include additional elements. For example, the expression vector can have one or two replication systems, thus allowing it to be maintained, for example, in plant or insect cells for expression and in a prokaryotic host for cloning and amplification. In addition, the expression construct can contain a selectable marker gene to allow the selection of transformed host cells. Selection genes are known in the art and vary depending on the host cell used.

Expression vectors provided herein contain the aforementioned nucleic acids and/or polynucleotides. Such expression vectors can contain promoters (e.g., T7 promoter, T3 promoter, SP6 promoter, *E. coli* RNA polymerase promoter, lac promoter and its derivatives, tac promoter, trp promoter, the arabinose-inducible PBAD promoter, the L-rhamnose-inducible rhaPBAD promoter, bacteriophage lambda promoters (e.g, PL), CMV promoter, SV40 promoter, PGK promoter, EF-1 alpha promoter), operators, transcription termination signals (e.g., SV40 termination signal), splice sites (e.g., SV40 splice sites, beta-globin splice site), ribosome binding sites, signal sequences (e.g., immunoglobulin kappa signal sequence), epitopes tags (e.g., myc, FLAG), purification tags (e.g., His6), replication origins and drug selection markers. Linker sequences, encoding linker amino acids and/or comprising restriction enzyme recognition sites, or any other type of linker sequence, can also be operably linked to the nucleic acid encoding the subject polypeptide present in the vectors disclosed herein.

Cosmid libraries can be prepared by methods known in the art. See, for example, Maniatis et al. Molecular Cloning: A Laboratory Manual. Cold Spring Harbor Press, 2nd edition, 1989 and Sambrook et al., 2001. Such a library can be used for sequence-based screening and for any type functional screening of cells, or of supernatants, whole cell broths, cell-free lysates, or extracts derived from the cells. High throughput biological assays for herbicidal screening, enzymatic activities, anti-cancer activity, etc. are known in the art and described in the literature. See also Examples 7-11 herein.

Host Cells

The present disclosure further contemplates recombinant host cells containing an exogenous polynucleotide. Said polynucleotide can comprise one or more fragments of the *C. subtsugae* genes as disclosed herein, or can encode one or more of the polypeptides of the present disclosure. Host cells can be procaryotic (e.g., bacterial) or eucaryotic (e.g., yeast, insect, mammalian). The host can also be a synthetic cell.

In certain embodiments, the host cell is a microorganism. Suitable microorganisms are those capable of colonizing plant tissue (e.g. root, stems, leaves, flowers, internally and on the surface), or the rhizosphere, in such manner that they come in contact with insect pests. Some of the host microorganisms can also be capable of colonizing the gut of an insect pest, and be capable of being transmitted from one insect to another. Host microorganisms can also colonize the gut and body surface of a plant pest. The host cell can also be used as a microbial factory for the production of *C. subtsugae* proteins, or for production of one or more compounds produced by the activity of *C. subtsugae* proteins such as, for example, peptides, lipids, lipopeptides, glycoproteins, secondary metabolites, antibiotics and small organic compounds.

Gram-negative microorganisms suitable for heterologous expression include: *Escherichia coli* (e.g., *E. coli* K12, *E. coli* BL21), *Pseudomonas* sp. (e.g. *Pseudomonas fluorescens, Pseudomonas putida, Psuedomonas aurantiaca, Psuedomonas aureofaciens, Psuedomonas protegens*), *Enterobacter* sp. (e.g. *Enterobacter cloacae*), and *Serratia* sp. Exemplary *E. coli* strains include *E. coli* BL21 and *E. coli* K12 for routine expression. Other *E. coli* strains, for more specialized purposes, are those which display protease deficiency (BL21-B838) and those which overexpress membrane proteins such as the BL21 derivative DF3, C41 (DF3) and C43 (DF3).

Methods for high-level expression of heterologous proteins in *E. coli* are known and include (a) IPTG-induction methods, (b) auto-induction methods, and (c) high cell-density IPTG-induction methods. See, for example, Sivashanmugam et al. (2009).

Gram-positive microorganisms suitable for heterologous expression include *Bacillus* sp. (e.g., *Bacillus megaterium, Bacillus subtilis, Bacillus cereus*), and *Streptomyces* sp. One advantage of using *Bacillus* as an expression host is that members of this genus produce spores, which provide formulations with better stability and longer shelf life. Expression systems based on *Bacillus megaterium* and *Bacillus subtilis* are commercially available from MoBiTec (Germany). Nucleotide sequences of interest can be expressed in *Bacillus megaterium* using under the control of the promoter of the xylose operon.

Fungal microorganisms suitable for heterologous expression include *Trichoderma* sp., *Gliocadium, Saccharomyces cerevisiae*, and *Pichia pastoris*. Heterologous DNA can be introduced into filamentous fungi by protoplast-mediated transformation using polyethylene glycol (PEG) or by electroporation-based methods. Particle bombardment is another method that has been successfully used to transform fungal cells.

Methods and compositions for transformation of *Saccharomyces cerevisiae* are known in the art. For example, a nucleic acid can be cloned into a suitable vector (e.g., the YES vectors (Invitrogen, Carlsbad, Calif.), under the control of an inducible promoter such as GAL1, and the CYC1 terminator, and expressed in *Saccharomyces cerevisiae*. The resulting cells can be tested for the desired activity, or for protein expression.

Heterologous expression can also be conducted in other yeast species (Jeffries et al., 2010), such as *Pichia pastoris, Hansenula polymorpha, Arxula adenivorans* and *Yarrowia lipolytica*. Transformation of *Pichia pastoris* can be achieved with the use of a commercial kit, such as the PichiaPink Expression System (Invitrogen, Carlsbad, Calif.), the *Pichia* Classic Protein Expression System or the *Pichia* GlycoSwitch (for glycosylated proteins) (Research Corporation Technologies, Tucson, Ariz.). For transformation of the yeasts *Pichia pastoris* or *Hansenula. polymorpha*, electroporation can also be used.

In certain embodiments, non-pathogenic symbiotic bacteria, which are able to live and replicate within plant tissues (i.e., endophytes), or non-pathogenic symbiotic bacteria, which are capable of colonizing the phyllosphere or the rhizosphere (i.e., epiphytes) are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*.

Symbiotic fungi, such as *Trichoderma* and *Gliocladium* can also be used as hosts for propagation and/or expression of the sequences disclosed herein.

Formulations and Pesticidal Compositions

The present disclosure provides pesticidal (e.g., insecticidal) compositions and formulations comprising the nucleic acids and polypeptides disclosed herein.

A "pest" is an organism (prokaryotic, eucaryotic or Archael) that increases mortality and/or slows, stunts or otherwise alters the growth of a plant. Pests include, but are not limited to, nematodes, insects, fungi, bacteria, and viruses.

A "pesticide" as defined herein, is a substance derived from a biological product, or a chemical substance, that increases mortality and/or inhibits the growth rate of plant pests. Pesticides include but are not limited to nematocides, insecticides, herbicides, plant fungicides, plant bactericides, and plant viricides.

A "biological pesticide" as defined herein is a microorganism with pesticidal properties.

A "pesticidal composition" is a formulation comprising a pesticide and optionally one or more additional components. Additional components include, but are not limited to, solvents (e.g., amyl acetate, carbon tetrachloride, ethylene dichloride; kerosene, xylene, pine oil, and others listed in EPA list 4a and 4b etc.), carriers, (e.g., organic flour, Walnut shell flour, wood bark), pulverized mineral (sulfur, diatomite, tripolite, lime, gypsum talc, pyrophyllite), clay (attapulgite bentonites, kaolins, volcanic ash, and others listed in EPA list 4a and 4b), stabilizers, emulsifiers (e.g., alkaline soaps, organic amines, sulfates of long chain alcohols and materials such as alginates, carbohydrates, gums, lipids and proteins, and others listed in EPA list 4a and 4b), surfactants (e.g., those listed in EPA list 4a and 4b), anti-oxidants, sun screens, a second pesticide, either chemical or biological (e.g., insecticide, nematicide, miticide, algaecide, fungicide, bactericide), an herbicide an/or an antibiotic.

A "carrier" as defined herein is an inert, organic or inorganic material, with which the active ingredient is mixed or formulated to facilitate its application to plant or other object to be treated, or its storage, transport and/or handling.

Pesticidal compositions as disclosed herein are useful for modulating pest infestation in a plant. The term "modulate" as defined herein is used to mean to alter the amount of pest infestation or rate of spread of pest infestation. Generally, such alteration is a lowering of the degree and/or rate and/or spread of the infestation.

The term "pest infestation" as defined herein, is the presence of a pest in an amount that causes a harmful effect including a disease or infection in a host population or emergence of an undesired weed in a growth system. Exemplary plant pests include, but are not limited to, mites (e.g., *Tetranychus urticae* (Two-spotted spider mite)), fruit flies (e.g., *Drosophila suzukii, Drosophila melanogaster*), house flies (e.g., *Musca domestica*), arachnids (e.g., *Acari* spp.), root maggots (*Anthomyidae* spp., e.g. Cabbage Root Maggots), aphids (e.g., *Myzus persicae* (green peach aphid)), *Triozidae* spp. (e.g., potato psyllid (*Bactericera cockerelli*)), beetles (*Tenebrionidae* spp., e.g., litter beetles (*Alphitobius diaperinus*)), grubs (e.g., white grub (*Cyclocephala lurida*), Southern Masked Chafer (*Rhizotrogus majalis*), Japanese beetle (*Popillia japonica*) larvae, black vine weevil (*Otiorhyncus sulcatus*) larvae, Oriental beetle (*Anomala orientalis*) larvae, scarabs (e.g., *Scarabaeidae* spp.), nematodes (e.g., Root-knot nematode (*Meloidogyne* spp.)), fungi, bacteria, and various plant viruses, for example, Tobacco mosaic virus, Tomato spotted wilt virus, Tomato yellow leaf curl virus, Cucumber mosaic virus, Potato virus Y, Cauliflower mosaic virus, African cassava mosaic virus, Plum pox virus, Brome mosaic virus, Potato virus X, Citrus tristeza virus, Barley yellow dwarf virus, Potato leaf roll virus and Tomato bushy stunt virus.

Pesticidal compositions, as disclosed herein, can be used either for prophylactic or modulatory purposes. When provided prophylactically, the compositions(s) are provided in advance of any symptoms of infestation. The prophylactic administration of the composition(s) serves to prevent, attenuate, or decrease the rate of onset of any subsequent infection or infestation. When provided for modulatory purposes, the composition(s) are provided at (or shortly after) the onset of an indication of infection or infestation. Modulatory administration of the compound(s) serves to attenuate the pathological symptoms of the infection or infestation and to increase the rate of recovery.

Additional methods can be employed to control the duration of action. Controlled-release can be achieved through the use of polymers to complex or absorb one or more of the components of the composition. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate compositions as disclosed herein into particles of a polymeric material such as polyesters, polyamino acids, hydrogels, poly(lactic acid) or ethylene vinylacetate copolymers. Alternatively, instead of incorporating these compositions into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal delivery systems, for example, liposomes, albumin microspheres, microemulsions, nanoparticles, and nanocapsules or in macroemulsions. Such techniques are known in the art.

Pesticidal compositions as disclosed herein, (e.g., pesticidal toxins) can be produced by expression of selected *Chromobacterium subtsugae* gene sequences in heterologous hosts suitable for lab scale, pilot scale and manufacturing scale fermentation (e.g., *E. coli, Psuedomonas* sp., yeast, etc.). Toxins can be produced by fermentation procedures known in the art using the heterologous host and formulated directly, or after extraction and purification of the toxin from the fermentation broth. The formulation can include live cells or non-viable cells.

The pesticidal compositions disclosed herein can be formulated in any manner. Non-limiting formulation examples include, but are not limited to, emulsifiable concentrates (EC), wettable powders (WP), soluble liquids (SL), aerosols, ultra-low volume concentrate solutions (ULV), soluble powders (SP), microencapsulates, water dispersed granules, flowables (FL), microemulsions (ME), nano-emulsions (NE), etc. In any of the formulations described herein, the percentage of the active ingredient is within a range of 0.01% to 99.99%. Detailed description of pesticide formulations can be found in the Kirk-Othmer Encyclopedia of Chemical Technology; Knowles, A. 2005. New Developments in Crop Protection Product Formulation, A grow Reports, London, UK; Valkenburg, W. van (ed.) 1973, Pesticide Formulation, Marcel Dekker, New York, USA; Knowles, D. A. (ed.) 1998, Chemistry and Technology of Agrochemical Formulations, Kluwer Academic Publishers, Dordrecht, the Netherlands.

Powder and Dust Formulations

These are simple formulations that usually contain 0.1-25% of the active ingredient. However, higher concentrations of active ingredient can be used depending on the potency and particular application. The pesticide toxin is mixed with a solid carrier, preferably of small particle size. Solid carriers can include: silicate clays (e.g., attapulgite, bentonites, volcanic ash, montmorillionite, kaolin, talc, diatomites, etc.), carbonates (e.g., calcite, dolomite, etc), synthetics (precipitated silica, fumed silica, etc.), ground botanicals (e.g., corn cob grits, rice hulls, coconut shells, etc.), organic flour (e.g., Walnut shell flour, wood bark, etc.) or pulverized mineral (e.g., Sulphur, diatomite, tripolite, lime, gypsum talc, pyrophyllite, etc.). The inert ingredients used in dust formulations can also come from those listed in EPA Inert List 4a (www.epa.gov/opprd001/inerts/inerts_list4Acas.pdf) for conventional formulations and 4b (www.epa.gov/opprd001/inerts/inerts_list4Bname.pdf) for organic formulations. Small particle size can be achieved by mixing the active ingredient with the carrier and pulverizing in a mill. Dusts are defined as having a particle size less than 100 microns; and with increase in particle size the toxicity of the formulation decreases. In the selection of a dust formulation its compatibility, fineness, bulk density, flow ability, abrasiveness, absorbability, specific gravity and cost should be taken into consideration. Exemplary dust formulations are provided in Table 1.

TABLE 1

| Formulation components | Formulation A | Formulation B | Formulation C | Formulation D |
|---|---|---|---|---|
| Active ingredient | 0.65 | 5 | 10 | 25 |
| Talc | 50 | | 90 | |
| Kaolin or other clay | 49.35 | 95 | | 75 |

A dust formulation can also be prepared from a dust concentrate (e.g., 40% active ingredient, 5% stabilizer, 20% silica, 35% magnesium carbonate) added at 1-10% to a 1:1 organic filler/talc combination.

The dust formulation is used as a contact powder (CP) or tracking powder (TP) against crawling insects.

A dust formulation with high flowability can be applied by pneumatic equipments in greenhouses.

Granular and Pellet Formulations

The pesticidal toxin is applied in liquid form to coarse particles of porous material (e.g., clay, walnut shells, vermiculite, diatomaceous earth, corn cobs, attapulgite, montmorillioinite, kaolin, talc, diatomites, calcite, dolomite, silicas, rice hulls, coconut shells, etc.). The granules or pellets can be water dispersible, and can be formed by extrusion (for pesticidal actives with low water solubility), agglomeration or spray drying. Granules can also be coated or impregnated with a solvent-based solution of the pesticidal toxin. The carrier particles can be selected from those listed in EPA Inert List 4a (www.epa.gov/opprd001/inerts/inerts_list4Acas.pdf) for conventional formulations and 4b (www.epa.gov/opprd001/inerts/inerts_list4Bname.pdf) for organic formulations. The active ingredient can be absorbed by the carrier material or coated on the surface of the granule. Particle size can vary from 250 to 1250 microns (0.25 mm to 2.38 mm) in diameter. The formulations usually contain 2 to 10 percent concentration of the toxicant. The granules are applied in water or whorls of plant or to soil at the rate of 10 kg/ha. Granular formulations of systemic insecticides are used for the control of sucking and soil pest by application to soil. Whorl application is done for the control of borer pests of crops such as sorghum, maize and sugarcane, etc. These types of formulations reduce drift and allow for slower release of the pesticidal composition.

Granular pesticides are most often used to apply chemicals to the soil to control weeds, fire ants, nematodes, and insects living in the soil or for absorption into plants through the roots. Granular formulations are sometimes applied by airplane or helicopter to minimize drift or to penetrate dense vegetation. Once applied, granules release the active ingredient slowly. Some granules require soil moisture to release the active ingredient. Granular formulations also are used to control larval mosquitoes and other aquatic pests. Granules are used in agricultural, structural, ornamental, turf, aquatic, right-of-way, and public health (biting insect) pest control operations.

Application of granular formulations is common in pre-emergence herbicides or as soil insecticides for direct application and incorporation into soil or other solid substrates where plants grow. Granules or pellets can also be applied in-furrow. Granules are commonly used for application to water, such as in flooded rice paddies.

A typical granule formulation includes (% w/w) 1-40% active ingredient, 1-2% stabilizer, 0-10% resin or polymer, 0-5% surfactant, 0-5% binder and is made up to 100% with the carrier material.

Wettable Powder Formulations

Wettable powder is a powdered formulation which yields a rather stable suspension when diluted with water. It is formulated by blending the pesticidal agent with diluents such as attapulgite, a surface active agent and auxiliary materials such as sodium salts of sulfo acids. Optionally stickers are added to improve retention on plants and other surfaces. Wettable powders can be prepared by mixing the pesticidal toxin (10-95%) with a solid carrier, plus 1-2% of a surface-active agent to improve suspensibility. The overall composition of the formulation includes the active ingredient in solid form (5.0-75%), an anionic dispersant and an anionic or nonionic wetting agent.

A typical example of a wettable powder formulation includes 10-80% active ingredient, 1-2% wetting agents (e.g., benzene sulphonates, naphthalene sulphonates, aliphatic suplhosuccinates, aliphatic alcohol etoxylates, etc.), 2-5% dispersing agent (e.g., lignosulphonates, naphthalene sulphonate-formaldehyde condensates, etc.), and 0.1-1% antifoaming agent (e.g., isopar M (Exxon/Mobil)), made up to 100% with an inert filler or carrier (e.g., diatomaceous earth, silica, etc.).

Emulsifiable Concentrate (EC) Formulations

These are concentrated pesticide formulation containing an organic solvent and a surfice-active agent to facilitate emulsification with water. When EC formulations are sprayed on plant parts, the solvent evaporates quickly, leaving a deposit of toxin from which water also evaporates. Exemplary emulsifying agents in insecticide formulations include alkaline soaps, organic amines, sulfates of long chain alcohols and materials such as alginates, carbohydrates, gums, lipids and proteins. Emulsifying agents can be selected from those listed in EPA Inert List 4a (www.epa.gov/opprd001/inerts/inerts_list4Acas.pdf) for conventional formulations and 4b (www.epa.gov/opprd001/inerts/inerts_list4Bname.pdf) for organic formulations.

Solution Formulations

A solution formulation is a concentrated liquid pesticide formulation that can be used directly, or require dilution in the case of a soluble concentrate. Soluble concentrates and solutions are water- or solvent-based mixtures with complete miscibility in water.

A typical example of a solution concentrate formulation includes 20-70% active ingredient, 5-15% wetting agent, 5-10% antifreeze, and is made up to 100% with water or a water miscible solvent.

Depending on the nature and stability of the pesticidal toxin, a solution formulation can optionally include thickeners, preservatives, antifoam, pH buffers, UV screens, etc.

Aerosol and Fumigant Formulations

In an insecticidal aerosol, the toxin is suspended as minute particles having sizes ranging from 0.1 to 50 microns in air as a fog or mist. This is achieved by burning the toxin or vaporizing it by heating. The toxicant dissolved in a liquefied gas, if released through small hole, may cause the toxicant particles to float in air with the rapid evaporation of the released gas.

A chemical compound, which is volatile at ambient temperatures and sufficiently toxic, is known as a fumigant. Fumigants generally enter an insect via its tracheal system. Fumigants are used for the control of insect pests in storage bins, buildings and certain insects and nematodes in the soil. Most fumigants are liquids held in cans or tanks and often comprise mixtures of two or more gases. Alternatively, phosphine or hydrogen phosphide gas can be generated in the presence of moisture from a tablet made up of aluminium phosphide and ammonium carbonate. The advantage of using a fumigant is that sites that are not easily accessible to other chemicals can be reached with fumigants, due to the penetration and dispersal of the gas. Commonly used fumigants are EDCT, methyl bromide, aluminium phosphide and hydrocynic acid.

Formulation in Fertilizers Mixtures

A fertilizer mixture can be manufactured by addition of an insecticidal composition, as disclosed herein, to a chemical fertilizer, or by spreading the composition directly on the fertilizer. Fertilizer mixtures are applied at the regular fertilizing time and provide both plant nutrients and control of soil insects. In an exemplary fertilizer formulation, urea (2% solution) is mixed with an insecticidal composition and sprayed for supply of nitrogen to the plant and for realizing effective pest control.

Formulation as Poison Baits.

Poison baits consist of a base or carrier material attractive to the pest species and a chemical toxicant in relatively small quantities. The poison baits are used for the control of fruit flies, chewing insects, wireworms, white grubs in the soil, household pests, rats in the field and slugs. These formulations are useful for situations in which spray application is difficult. A common base used in dry baits is wheat bran moistened with water and molasses. For the control of fruit sucking moths fermenting sugar solution or molasses with a toxin is used.

Formulations for Seed Treatments

Seed treatments include application of a pesticidal composition, optionally in combination with other bioactive, antagonistic or symbiotic agents, to the surface of a seed prior to sowing. The pesticidal toxins, proteins, and/or compounds disclosed herein can be formulated for seed treatments in any of the following modes: dry powder, water slurriable powder, liquid solution, flowable concentrate or emulsion, emulsion, microcapsules, gel, or water dispersible granules; or can be applied to seeds by spraying on the seed before planting.

In the case of a dry powder, the active ingredient is formulated similarly to a wettable powder, but with the addition of a sticking agent, such as mineral oil, instead of a wetting agent. For example: one kg of purified talc powder (sterilized for 12 h), 15 g calcium carbonate, and 10 g carboxymethyl cellulose are mixed under aseptic conditions following the method described by Nandakumar et al (2001). Protein, nucleic acid suspensions or organisms expressing these are mixed in a 1:2.5 ratio (suspension to dry mix) and the product is shade dried to reduce moisture content to 20-35%.

The compositions can be in the form of a liquid, gel or solid.

A solid composition can be prepared by suspending a solid carrier in a solution of active ingredient(s) and drying the suspension under mild conditions, such as evaporation at room temperature or vacuum evaporation at 65° C. or lower. For liquid compositions, the active ingredient can be dissolved in a suitable carrier or solvent.

A composition can comprise gel-encapsulated active ingredient(s). Such gel-encapsulated materials can be prepared by mixing a gel-forming agent (e.g., gelatin, cellulose, or lignin) with a composition comprising one or more nucleic acids and/or polypeptides as disclosed herein, and optionally a second pesticide or herbicide; and inducing gel formation of the agent.

The composition can additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) monolaurate. The concentration of surfactants can range between 0.1-35% of the total formulation, e.g., from 5-25%. The choice of dispersing and emulsifying agents, such as non-ionic, anionic, amphoteric and cationic dispersing and emulsifying agents, and the amount employed, is determined by the nature of the composition and the ability of the agent to facilitate the dispersion of the composition.

Formulations Comprising Microorganisms

Pesticidal compositions as set forth above can be combined with a microorganism. The microorganism can be a plant growth promoter. Suitable microorganisms include, but are not limited to, *Bacillus* sp. (e.g., *Bacillus firmus, Bacillus thuringiensis, Bacillus pumilus, Bacillus licheniformis, Bacillus amyloliquefaciens, Bacillus subtilis*), *Paecilomyces* sp. (*P. lilacinus*), *Pasteuria* sp. (*P. penetrans*), *Pseudomonas* sp., *Brevabacillus* sp., *Lecanicillium* sp., *Ampelomyces* sp., *Pseudozyma* sp., *Streptomyces* sp (*S. bikiniensis, S. costaricanus, S. avermitilis*), *Burkholderia* sp., *Trichoderma* sp., *Gliocladium* sp., avermectin, *Myrothecium* sp., *Paecilomyces* spp., *Sphingobacterium* sp., *Arthrobotrys* sp., *Chlorosplenium* sp., *Neobulgaria* sp., *Daldinia* sp., *Aspergillus* sp., *Chaetomium* sp., *Lysobacter* sp., *Lachnum papyraceum, Verticillium suchlasporium, Arthrobotrys oligospora, Verticillium chlamydosporium, Hirsutella rhossiliensis, Pochonia chlamydosporia, Pleurotus ostreatus, Omphalotus olearius, Lampteromyces japonicas, Brevudimonas* sp., *Muscodor* sp., *Photorhabdus* sp., and *Burkholderia* sp. Agents obtained or derived from such microorganisms can also be used in combination with the pesticidal nucleic acids and polypeptides disclosed herein.

Formulations Comprising Second Pesticides

Pesticidal compositions as set forth above can be combined with a second pesticide (e.g., nematocide, fungicide, insecticide, algaecide, miticide, or bactericide). Such an agent can be a natural oil or oil-product having fungicidal, bactericidal, nematicidal, acaricidal and/or insecticidal activity (e.g., paraffinic oil, tea tree oil, lemongrass oil, clove oil, cinnamon oil, citrus oil, rosemary oil, pyrethram). Furthermore, the pesticide can be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine); a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, an anthranilic diamide (e.g., chlorantranilipole) and a quinone outside inhibitor (e.g., strobilurin). The strobilurin may include but is not limited to azoxystrobin, kresoximmethoyl or trifloxystrobin. In yet another particular embodiment, the anti-fungal agent is a quinone, e.g., quinoxyfen (5,7-dichloro-4-quinolyl 4-fluorophenyl ether). The anti-fungal agent can also be derived from a *Reynoutria* extract.

The fungicide can also be a multi-site non-inorganic, chemical fungicide selected from the group consisting of chloronitrile, quinoxaline, sulphamide, phosphonate, phosphite, dithiocarbamate, chloralkythios, phenylpyridinamine, and cyano-acetamide oxime.

The composition can, as noted above, further comprise an insecticide. The insecticide can include but is not limited to avermectin, Bt (e.g., *Bacillus thuringiensis* var. kurstaki), neem oil, spinosads, *Burkholderia* sp. (e.g., as set forth in WO2011/106491), entomopathogenic fungi such a *Beauveria bassiana* and chemical insecticides including but not limited to organochlorine compounds, organophosphorous compounds, carbamates, pyrethroids, pyrethrins and neonicotinoids.

As noted above, the composition may further comprise a nematocide. This nematocide may include, but is not limited to, avermectin, microbial products such as Biome (*Bacillus firmus*), *Pasteuria* spp and organic products such as saponins.

Methods for Modulating Pest Infestation

Thus, according to the present disclosure, methods for modulating pest infestation in a plant are provided. The methods comprise application to a plant, or to the soil or substrate in which the plant is growing, of a pesticidal composition comprising a nucleic acid as disclosed herein; i.e., any of SEQ ID NOs:4-6.

Additional methods for modulating pest infestation in a plant comprise application, to a plant, or to the soil or substrate in which the plant is growing, of a pesticidal composition comprising a polypeptide as disclosed herein; i.e., any of SEQ ID NOs:1-3.

When used as biological insect control agents, insecticidal toxins encoded by the *C. subtsugae* genome can be produced by expression of a *C. subtsugae* nucleotide sequence in a heterologous host cell capable of expressing the nucleotide sequences. In one embodiment, one or more *C. subtsugae* nucleotide sequences are inserted into an appropriate expression cassette comprising, e.g., a promoter and a transcriptional termination signal. Expression of the nucleotide sequence(s) can be constitutive or inducible, depending on the promoter and/or external stimuli. In certain embodiments, the cell in which the toxin is expressed is a microorganism, such as a virus, a bacterium, or a fungus.

In certain embodiments, a virus, such as a baculovirus, is engineered to contain a

*C. subtsugae* nucleotide sequence in its genome. Such a recombinant virus can express large amounts of, e.g., an insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in vivo and kill them, either by expression of the insecticidal toxin or by a combination of viral infection and expression of the insecticidal toxin.

Thus, the compositions set forth above, comprising *C. subtsugae* nucleic acids and polypeptides, can be used as pesticides. In particular, the compositions as set forth above can be used as, for example, insecticides and nematicides, alone or in combination with one or more second pesticidal substances as set forth herein.

Specifically, nematodes that may be controlled using the method set forth above include but are not limited to parasitic nematodes such as root-knot, cyst, and lesion nematodes, including but not limited to seed gall nematodes (*Afrina wevelli*), bentgrass nematodes (*Anguina agrostis*), shoot gall nematodes (*Anguina* spp.), seed gall nematodes (*Anguina* spp., *A. amsinckiae, A. balsamophila; A. tritici*), fescue leaf gall nematodes (*A. graminis*), ear-cockle (or wheat gall) nematodes (*Anguina tritici*), bud and leaf (or foliar) nematodes (*Aphelenchoides* spp., *A. subtenuis*), begonia leaf (or fern, or spring crimp, or strawberry foliar, or strawberry nematodes, or summer dwarf) nematodes (*A. fragariae*), fern nematodes (*A. olesistus*), rice nematodes (*A. oryzae*), currant nematodes (*A. ribes*), black currant (or chrysanthemum) nematodes (*A. ritzemabosi*), chrysanthemum foliar or leaf nematodes (*A. ritzemabosi*), rice white-tip (or spring dwarf, or strawberry bud) nematodes (*A. besseyi*), fungus-feeding (mushroom) nematodes (*Aphelenchoides composticola*), *Atalodera* spp. (*Atalodera lonicerae, Atalodera ucri*), spine nematodes (*Bakernema variabile*), sting nematodes (*Belonolaimus* spp., *B. gracilis, B. longicaudatus*), pine wood nematodes (*Bursaphelenchus* spp., *B. xylophilus, B. mucronatus*), sessile nematodes (*Cacopaurus* spp., *C. epacris, C. pestis*), amaranth cyst nematodes (*Cactodera amaranthi*), birch cyst nematodes (*C. betulae*), cactus cyst nematodes (*C. cacti*), estonian cyst nematodes (*C. estonica*), Thorne's cyst nematodes (*C. thornei*), knotweed cyst nematodes (*C. weissi*), ring nematodes (*Criconema* spp.), spine nematodes (*Criconema* spp., *C. civellae, C. decalineatum, C. spinalineatum*), ring nematodes (*Criconemella axeste, C. curvata, C. macrodora, C. parva*), ring nematodes (*Criconemoides* spp., *C. citri, C. simile*), spine nematodes (*Crossonema fimbriatum*), eucalypt cystoid nematodes (*Cryphodera eucalypti*), bud, stem and bulb nematodes (*Ditylenchus* spp., *D. angustus, D.* dipsaci, *D.* destructor, *D. intermedius*), Mushroom spawn nematodes (*D. myceliophagus*), awl nematodes (*Dolichodorus* spp., *D. heterocephalus, D. heterocephalous*), spear nematodes (*Dorylaimus* spp.), stunt nematodes (*Geocenamus superbus*), cyst nematodes (*Globodera* spp.), yarrow cyst nematodes (*G. achilleae*), milfoil cyst nematodes (*G. millefolii*), apple cyst nematodes (*G. mali*), white cyst potato nematodes (*G. pallida*), golden nematodes (*G. rostochiensis*), tobacco cyst nematodes (*G. tabacum*), Osborne's cyst nematodes (*G. tabacum solanacearum*), horsenettle cyst nematodes (*G. tabacum virginiae*), pin nematodes (*Gracilacus* spp., *G. idalimus*), spiral nematodes (*Helicotylenchus* spp., *H. africanus, H. digonicus, H. dihystera, H. erythrinae, H. multicinctus, H. paragirus, H. pseudorobustus, H. solani, H. spicaudatus*), sheathoid nematodes (*Hemicriconemoides* spp., *H. biformis, H. californianus, H. chitwoodi, H. floridensis, H. wessoni*), sheath nematodes (*Hemicycliophora* spp., *H. arenaria, H. biosphaera, H. megalodiscus, H. parvana, H. poranga, H. sheri, H. similis, H. striatula*), cyst nematodes (*Heterodera* spp.), almond cyst nematodes (*H. amygdali*), oat (or cereal) cyst nematodes (*H. avenae*), *Cajanus* (or pigeon pea) cyst nematodes (*H. cajani*), bermudagrass (or heart-shaped, or Valentine) cyst nematodes (*H. cardiolata*), carrot cyst nematodes (*H. carotae*), cabbage cyst nematodes or *brassica* root eelworm (*H. cruciferae*), nutgrass (or sedge) cyst nematodes (*H. cyperi*), Japanese cyst nematodes (*H. elachista*), fig (or ficus, or rubber) cyst nematodes (*H. fici*), galeopsis cyst nematodes (*H. galeopsidis*), soybean cyst nematodes (*H. glycines*), alfalfa root (or pea cyst) nematodes (*H. goettingiana*), buckwheat cyst nematodes (*H. graduni*), barley cyst nematodes (*H. hordecalis*), hop cyst nematodes (*H. humuli*), Mediterranean cereal (or wheat) cyst nematodes (*H. latipons*), lespedeza cyst nematodes (*H. lespedezae*), Kansas cyst nematodes (*H. longicolla*), cereals root eelworm or oat cyst nematodes (*H. major*), grass cyst nematodes (*H. mani*), lucerne cyst nematodes (*H. medicaginis*), cyperus (or motha) cyst nematodes (*Heterodera mothi*), rice cyst nematodes (*H. oryzae*), Amu-Darya (or camel thorn cyst) nematodes (*H. oxiana*), dock cyst nematodes (*H. rosii*), *rumex* cyst nemtodes (*H. rumicis*), sugar beet cyst nematodes (*H. schachtii*), willow cyst nematodes (*H. salixophila*), knawel cyst nematodes (*H. scleranthii*), sowthistle cyst nematodes (*H. sonchophila*), tadzhik cyst nematodes (*H. tadshikistanica*), turkmen cyst nematodes (*H. turcomanica*), clover cyst nematodes (*H. trifolii*), nettle cyst nematodes (*H. urticae*), ustinov cyst nematodes (*H. ustinovi*), cowpea cyst nematodes (*H. vigni*), corn cyst nematodes (*H. zeae*), rice root nematodes (*Hirschmanniella* spp., *H. belli, H. caudacrena, H. gracilis, H. oryzae*), lance nematodes (*Hoplolaimus* spp.), Columbia nematodes (*H. columbus*), Cobb's lance nematodes (*H. galeatus*), crown-headed lance nematodes (*H. tylenchiformis*), pseudo root-knot nematodes (*Hypsoperine graminis*), needle nematodes (*Longidorus* spp., *L. africanus, L. sylphus*), ring nematodes (*Macroposthonia* (=*Mesocriconema*) *xenoplax*), cystoid nematodes (*Meloidodera* spp.), pine cystoid nematodes (*M. floridensis*), tadzhik cystoid nematodes (*M. tadshikistanica*), cystoid body nematodes (*Meloidoderita* spp.), stunt nematodes (*Merlinius* spp., *M. brevidens*, *M. conicus*, *M. grandis*, *M. microdorus*), root-knot nematodes (*Meloidogyne* spp., *M. acronea*, *M. arenaria*, *M. artiellia*, *M. brevicauda*, *M. camelliae*, *M. carolinensis*, *M. chitwoodi*, *M. exigua*, *M. graminicola*, *M. hapla*, *M. hispanica*, *M. incognita*, *M. incognita acrita*, *M. indica*, *M. inornata*, *M. javanica*, *M. kikuyuensis*, *M. konaensis*, *M. mali*, *M. microtyla*, *M. naasi*, *M. ovalis*, *M. platani*, *M. querciana*, *M. sasseri*, *M. tadshikistanica*, *M. thamesi*), knapweed nematodes (*Mesoanguina picridis*), Douglas fir nematodes (*Nacobbodera chitwoodi*), false root-knot nematodes (*Nacobbus aberrans*, *N. batatiformis*, *N. dorsalis*), sour paste nematodes (*Panagrellus redivivus*), beer nematodes (*P. silusiae*), needle nematodes (*Paralongidorus microlaimus*), spiral nematodes (*Pararotylenchus* spp.), stubby-root nematodes (*Paratrichodorus allius*, *P. minor*, *P. porosus*, *P. renifer*), pin nematodes (*Paratylenchus* spp., *P. baldaccii*, *P. bukowinensis*, *P. curvitatus*, *P. dianthus*, *P. elachistus*, *P. hamatus*, *P. holdemani*, *P. italiensis*, *P. lepidus*, *P. nanus*, *P. neoamplycephalus*, *P. similis*), lesion (or meadow) nematodes (*Pratylenchus* spp., *P. alleni*, *P. brachyurus*, *P. coffeae*, *P. convallariae*, *P. crenatus*, *P. flakkensis*, *P. goodeyi*, *P. hexincisus*, *P. leiocephalus*, *P. minyus*, *P. musicola*, *P. neglectus*, *P. penetrans*, *P. pratensis*, *P. scribneri*, *P. thornei*, *P. vulnus*, *P. zeae*), stem gall nematodes (*Pterotylenchus cecidogenus*), grass cyst nematodes (*Punctodera punctate*), stunt nematodes (*Quinisulcius acutus*, *Q. capitatus*), burrowing nematodes (*Radopholus* spp.), banana-root nematodes (*R. similis*), rice-root nematodes (*R. oryzae*), red ring (or coconut, or cocopalm) nematodes (*Rhadinaphelenchus cocophilus*), reniform nematodes (*Rotylenchulus* spp., *R. reniformis*, *R. parvus*), spiral nematodes (*Rotylenchus* spp., *R. buxophilus*, *R. christiei*, *R. robustus*), Thorne's lance nematodes (*R. uniformis*), *Sarisodera hydrophylla*, spiral nematodes (*Scutellonema* spp., *S. blaberum*, *S. brachyurum*, *S. bradys*, *S. clathricaudatum*, *S. christiei*, *S. conicephalum*), grass root-gall nematodes (*Subanguina radicicola*), round cystoid nematodes (*Thecavermiculatus andinus*), stubby-root nematodes (*Trichodorus* spp., *T. christiei*, *T. kurumeensis*, *T. pachydermis*, *T. primitivus*), vinegar eels (or nematodes) (*Turbatrix aceti*), stunt (or stylet) nematodes (*Tylenchorhynchus* spp., *T. agri*, *T. annulatus*, *T. aspericutis*, *T. claytoni*, *T. ebriensis*, *T. elegans*, *T. golden*, *T. graciliformis*, *T. martini*, *T. mashhoodi*, *T. microconus*, *T. nudus*, *T. oleraceae*, *T. penniseti*, *T. punensis*), citrus nematodes (*Tylenchulus semipenetrans*), and dagger nematodes (*Xiphinema* spp., *X. americanum*, *X. bakeri*, *X. brasiliense*, *X. brevicolle*, *X. chambersi*, *X. coxi*, *X. diversicaudatum* *X. index*, *X. insigne*, *X. nigeriense*, *X. radicicola*, *X. setariae*, *X. vulgarae*, *X. vuittenezi*).

Phytopathogenic insects controlled by the methods set forth above include but are not limited to non-Culicidae larvae insects from the order (a) Lepidoptera, for example, *Acleris* spp., *Adoxophyes* spp., *Aegeria* spp., *Agrotis* spp., *Alabama argillaceae*, *Amylois* spp., *Anticarsia gemmatalis*, *Archips* spp., *Argyrotaenia* spp., *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia binotalis*, *Cryptophlebia leucotreta*, *Cydia* spp., *Diatraea* spp., *Diparopsis castanea*, *Earias* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora gossypiella*, *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; (b) Coleoptera, for example, *Agriotes* spp., *Anthonomus* spp., *Atomaria linearis*, *Chaetocnema tibialis*, *Cosmopolites* spp., *Curculio* spp., *Dermestes* spp., *Diabrotica* spp., *Epilachna* spp., *Eremnus* spp., *Leptinotarsa decemlineata*, *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp-, *Scarabeidae*, *Sitophilus* spp., *Sitotroga* spp., *Tenebrio* spp., *Tribolium* spp. and *Trogoderma* spp.; (c) Orthoptera, for example, *Blatta* spp., *Blattella* spp., *Gryllotalpa* spp., *Leucophaea maderae*, *Locusta* spp., *Periplaneta* spp. and *Schistocerca* spp.; (d) Isoptera, for example, *Reticulitermes* spp.; (e) Psocoptera, for example, *Liposcelis* spp.; (f) Anoplura, for example, *Haematopinus* spp., *Linognathus* spp., *Pediculus* spp., *Pemphigus* spp. and *Phylloxera* spp.; (g) Mallophaga, for example, *Damalinea* spp. and *Trichodectes* spp.; (h) Thysanoptera, for example, *Frankliniella* spp., *Hercinotnrips* spp., *Taeniothrips* spp., *Thrips palmi*, *Thrips tabaci* and *Scirtothrips aurantii*; (i) Heteroptera, for example, *Cimex* spp., *Distantiella theobroma*, *Dysdercus* spp., *Euchistus* spp., *Eurygaster* spp., *Leptocorisa* spp., *Nezara* spp., *Piesma* spp., *Rhodnius* spp., *Sahlbergella singularis*, *Scotinophara* spp. and *Tniatoma* spp.; (j) Homoptera, for example, *Aleurothrixus floccosus*, *Aleyrodes brassicae*, *Aonidiella* spp., *Aphididae*, *Aphis* spp., *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp., *Laodelphax* spp., *Lecanium corni*, *Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri*; (k) Hymenoptera, for example, *Acromyrmex*, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Solenopsis* spp. and *Vespa* spp.; (l) Diptera, for example, *Aedes* spp., *Antherigona soccata*, *Bibio hortulanus*, *Calliphora erythrocephala*, *Ceratitis* spp., *Chrysomyia* spp., *Culex* spp., *Cuterebra* spp., *Dacus* spp., *Drosophila melanogaster*, *Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis pomonella*, *Sciara* spp., *Stomoxys* spp., *Tabanus* spp., *Tannia* spp. and *Tipula* spp.; (m) Siphonaptera, for example, *Ceratophyllus* spp. and *Xenopsylla cheopis* and (n) from the order Thysanura, for example, *Lepisma saccharina*.

The pesticidal compositions disclosed herein may further be used for controlling crucifer flea beetles (*Phyllotreta* spp.), root maggots (*Delia* spp.), cabbage seedpod weevil (*Ceutorhynchus* spp.) and aphids in oil seed crops such as canola (rape), mustard seed, and hybrids thereof, and also rice and maize. In a particular embodiment, the insect is a member of the *Spodoptera*, more particularly, *Spodoptera exigua*, *Myzus persicae*, *Plutella xylostella* or *Euschistus* sp.

Application of an effective pesticidal control amount of a pesticidal composition as disclosed herein is provided. Said pesticidal composition is applied, alone or in combination with another pesticidal substance, in an effective pest control or pesticidal amount. An effective amount is defined as that quantity of pesticidal composition, alone or in combination with another pesticidal substance that is sufficient to prevent or modulate pest infestation. The effective amount and rate can be affected by pest species present, stage of pest growth, pest population density, and environmental factors such as temperature, wind velocity, rain, time of day and seasonality. The amount that will be within an effective range in a particular instance can be determined by laboratory or field tests.

Methods of Application

The pesticidal compositions disclosed herein, when used in methods for modulating pest infestation, can be applied using methods known in the art. Specifically, these compositions can be applied to plants or plant parts by spraying, dipping, application to the growth substrate (e.g., soil) around the plant, application to the root zone, dipping roots prior to planting, application to plants as a turf or a drench, through irrigation, or as soil granules. Plants are to be understood as meaning in the present context all plants and plant populations such as desired and undesired wild plants or crop plants (including naturally occurring crop plants). Crop plants can be plants obtained by conventional plant breeding and optimization methods, by biotechnological and genetic engineering methods or by combinations of these methods, including transgenic plants and plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, off-shoots and seeds.

Application can be external, (e.g. by spraying, fogging or painting) or internal (e.g., by injection, transfection or the use of an insect vector). When applied internally, the compositions can be intracellular or extracellular (e.g., present in the vascular system of the plant, present in the extracellular space).

Treatment of the plants and plant parts with the compositions set forth above can be carried out directly or by allowing the compositions to act on a plant's surroundings, habitat or storage space by, for example, immersion, spraying, evaporation, fogging, scattering, painting on, injecting. In the case in which the composition is applied to a seed, the composition can be applied to the seed as one or more coats prior to planting the seed using methods known in the art.

Pesticidal compositions as disclosed herein can also be applied to seeds; e.g., as a seed coating. Different adherents ("stickers") can be used in the manufacture of seed coatings, including, for example, methyl cellulose, alginate, carrageenan and polyvinyl alcohol. The adherent is dissolved in water to a percentage between 1-10% and stored at room temperature before application to the seeds. Seeds are soaked in adherent solution (3 ml/100 seeds) for 15 min, scooped out and mixed with organic matter (1.5 g/100 seeds) in plastic bags and shaken vigorously. This process can also be automated using a seed coating machine.

For priming seeds with compositions as disclosed herein, seeds are soaked in twice the seed volume of sterile distilled water containing bacterial/protein/nucleic acid suspensions or talc formulation (dry formulation) (4-10 g kg of seed, depending on seed size) and incubated at 25±2° C. for 12-24 h. The suspension is then drained off and the seeds are dried under shade for 30 min and used for sowing.

The compositions can also be used as soil amendments, e.g., in combination with a carrier such as a talc formulation. Formulations for soil amendment can also include clays, emulsifiers, surfactants and stabilizers, as are known in the art. For preparation of talc based formulations, one kg of purified talc powder (sterilized for 12 h), 15 g calcium carbonate, and 10 g carboxymethyl cellulose are mixed under aseptic conditions following the method described by Nandakumar et al. (2001). Protein, nucleic acid suspensions or organisms expressing these are mixed in a 1:2.5 ratio (suspension to dry mix) and the product is shade-dried to reduce moisture content to 20-35%.

For soil amendment, formulations (e.g., talc formulations) can be applied at rates between 2.5-10 Kg ha-¹ at sowing and/or at different times after emergence, or both, depending on the crops.

The compositions disclosed herein can also be applied to soil using methods known in the art. See, for example, the USDA website at naldc.nal.usda.gov/download/43874/pdf, accessed Feb. 20, 2013. Such methods include but are not limited to fumigation, drip irrigation or chemigation, broadcast application of granules or sprays, soil incorporation (e.g., application of granules), soil drenching, seed treatment and dressing, and bare root dip.

Plant Transformation

The nucleic acids disclosed herein can be introduced into, and optionally expressed in, plants, using any of a number of plant transformation techniques. Transformation of plants can be undertaken with a single DNA species or multiple DNA species (i.e., co-transformation).

In certain embodiments, a *C. subtsugae* protein or polypeptide (e.g., a toxin) is expressed in a plant and provides protection to the plant from insect pests. For example, a nucleotide sequence as disclosed herein can be inserted into an expression cassette, which can optionally be stably integrated into the chromosome of a plant. In certain embodiments, the nucleotide sequence is included in a non-pathogenic self-replicating virus. Plants transformed in accordance with the present disclosure can be monocots or dicots and include but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, apricot, strawberry, papaya, avocado, mango, banana, alfalfa, rice, potato, eggplant, peach, cotton, carrot, tobacco, sorghum, nectarine, sugar beet, sugarcane, sunflower, soybean, tomato, pineapple, grape, raspberry, blackberry, cucumber, *Arabidopsis*, and woody plants such as coniferous and deciduous trees.

Once the desired nucleotide sequence has been introduced into a particular plant species, it can be propagated in that species, or transferred to other varieties of the same species, particularly including commercial varieties, using traditional breeding techniques.

DNA can be introduced into plant cells through the use of a number of art-recognized methods. Those skilled in the art will appreciate that the choice of methods can depend on the type of plant targeted for transformation. Suitable methods for transforming plant cells are as follows.

*Agrobacterium*-Mediated Transformation

A Cmajor method of DNA transfer in plants is *Agrobacterium* mediated transformation. The natural living soil bacterium *Agrobacterium tumefaciens* is capable of infecting a wide range of plant species, causing Crown Gall diseases. When *A. tumefaciens* infects a cell, it transfers a copy of its T-DNA, which is a small section of DNA carried on its Ti (Tumor Inducing) plasmid. The T-DNA is flanked by two (imperfect) 25 base pair repeats. Any DNA contained within these borders will be transferred to the host cell. Zupan and Zambriski, 1995. The T-DNA section on the Ti plasmid can be replaced by a transgene attached to an appropriate regulatory sequence(s). Recombinant *A. tumefaciens* containing a Ti plasmid comprising exogenous nucleotide sequences can then be used to infect cultures of either regenerating cell or protoplasts (i.e., wall-less spherical plant cells). Marker genes such as those coding for antibiotic resistance can be included in the Ti plasmid construct, so that it is possible to select cells that have been transformed by the bacterium. Cell-to-plant regeneration is carried out on the selected cells by standard methods. See, for example, Zupan and Zambriski (1995) and Jones et al. (2005) Plant Methods.

*Agrobacterium tumefaciens* can used to transform many dicotyledonous plant species with relative ease. Hinchee et al., Biotechnology 6:915-921 (1988). See also Ishida et al., Nature Biotechnology 14:745-750 (June 1996) for a description of maize transformation.

Biolistic Delivery

This method, also known as "particle bombardment," involves directly "shooting" a DNA molecule into the recipient plant tissue, using a "gene gun." Tungsten or gold beads (which are smaller than the plant cells themselves) are coated with the DNA of interest and fired through a stopping screen, accelerated by Helium, into the plant tissue. The particles pass through the plant cells, leaving the DNA inside. This method can be used on both monocotyledonous and dicotyledonous species successfully. Transformed tissue can be selected using marker genes such as those encoding antibiotic resistance. Whole plants, containing a copy of the transgene in all cells, can be regenerated from the totipotent transformed cells in culture (Nottingham, 1998), using devices available from Agracetus, Inc. (Madison, Wis.) and Dupont, Inc. (Wilmington, Del.).

Methods for biolistic plant transformation are known in the art. See, for example, Sanford et al., U.S. Pat. No. 4,945,050; McCabe et al., Biotechnology 6.923-926 (1988); Weissinger et al., Annual Rev Genet. 22-421-477 (1988); Sanford et al., Particulate Science and Technology 5.27-37 (1987)(onion); Svab et al., Proc. Natl. Acad. Sci. USA 87-8526-8530 (1990) (tobacco chloroplast); Christou et al., Plant Physiol 87,671-674 (1988)(soybean); McCabe et al., BioTechnology 6.923-926 (1988)(soybean); Klein et al., Proc. Natl. Acad. Sci. USA, 85:4305-4309 (1988)(maize); Klein et al., BioTechnology 6,559-563 (1988) (maize); Klein et al., Plant Physiol. 91,440 ddd (1988) (maize); Fromm et al., BioTechnology 8:833-839 (1990); Gordon-Kamm et al., Plant Cell 2: 603-618 (1990) (maize); Koziel et al., Biotechnology 11: 194-200 (1993) (maize); Shimamoto et al., Nature 338: 274-277 (1989) (rice); Christou et al., Biotechnology 9: 957-962 (1991) (rice); Datta et al., BioTechnology 8.736-740 (1990) (rice); European Patent Application EP 0 332 581 (orchardgrass and other Pooideae); Vasil et al., Biotechnology 11: 1553-1558 (1993) (wheat); Weeks et al., Plant Physiol. 102:1077-1084 (1993) (wheat); Wan et al., Plant Physiol. 104:37-48 (1994) (barley); Jahne et al., Theor. Appl. Genet. 89:525-533 (1994) (barley); Umbeck et al., BioTechnology 5:263-266 (1987) (cotton); Casas et al., Proc. Natl. Acad. Sci. USA 90:11212-11216 (December 1993) (sorghum); Somers et al., BioTechnology 10:1589-1594 (December 1992) (oat); Torbert et al., Plant Cell Reports 14:635-640 (1995) (oat); Weeks et al., Plant Physiol. 102:1077-1084 (1993) (wheat); Chang et al., WO 94/13822 (wheat) and Nehra et al., The Plant Journal 5:285-297 (1994) (wheat).

Methods for the introduction of recombinant DNA molecules into maize by microprojectile bombardment can be found in Koziel et al., Biotechnology 11: 194-200(1993), Hill et al., Euphytica 85:119-123 (1995) and Koziel et al., Annals of the New York Academy of Sciences 792:164-171 (1996).

Protoplast Transformation and Other Methods

Another method for the introduction of nucleic acid molecules into plants is the protoplast transformation method for maize as disclosed in EP 0 292 435. Additional delivery systems for gene transfer in plants include electroporation (Riggs et al., Proc. Natl. Acad, Sci. USA 83,5602-5606 (1986), microinjection (Crossway et al., BioTechniques 4,320-334 (1986), silicon carbide-mediated DNA transfer, direct gene transfer (Paszkowski et al., EMBO J. 3.2717-2722 (1984); Hayashimoto et al., Plant Physiol 93.857-863 (1990)(rice).

Plastid Transformation

In another embodiment, a nucleotide sequence as disclosed herein is directly transformed into the genome of a plastid (e.g., chloroplast). Advantages of plastid transformation include the ability of plastids to express bacterial genes without substantial modification of the bacterial sequences, and the ability of plastids to express multiple open reading frames under the control of a single promoter. Plastid transformation technology is described in U.S. Pat. Nos. 5,451,513; 5,545,817 and 5,545,818; in PCT application No. WO 95/16783, and in McBride et al. (1994) Proc. Natl. Acad. Sci. USA 91, 7301-7305.

The basic technique for chloroplast transformation involves introducing regions of cloned plastid DNA flanking a selectable marker, together with the gene of interest, into a suitable target tissue using, e.g., biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastid genome. Initially, point mutations in the chloroplast 16S rRNA and rps12 genes conferring resistance to spectinomycin and/or streptomycin were utilized as selectable markers for transformation (Svab, Z. et al. (1990) Proc. Natl. Acad. Sci. USA 87, 8526-8530; Staub, J. M., and Maliga, P. (1992) Plant Cell 4, 39-45); resulting in the production of stable homoplasmic transformants at a frequency of approximately one per 100 bombardments of target leaves. The presence of cloning sites between these markers allowed creation of a plastid targeting vector for introduction of foreign genes. Staub, J. M., and Maliga, P. (1993) EMBO J. 12: 601-606. Substantial increases in transformation frequency were obtained by replacement of the recessive rRNA or r-protein antibiotic resistance genes with a dominant selectable marker, the bacterial AADA gene encoding the spectinomycin-detoxifying enzyme aminoglycoside-3' adenyltransferase. Svab, Z., and Maliga, P. (1993) Proc. Natl. Acad. Sci. USA 90: 913-917. Previously, this marker had been used successfully for high-frequency transformation of the plastid genome of the green alga *Chlamydomonas reinhardtii*. Goldschmidt-Clermont, M. (1991) Nucl. Acids Res. 19: 4083-4089.

Other selectable markers useful for plastid transformation are known in the art and encompassed within the scope of the present disclosure. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage, compared to nuclear genes, to achieve expression levels that can readily exceed 10% of the total soluble plant protein. Thus, in certain embodiments, a nucleotide sequence as disclosed herein is inserted into a plastid targeting vector and transformed into the plastid genome of a desired plant host. Plants homoplastic for plastid genomes containing a nucleotide sequence of interest are obtained, and are capable of high-level expression of the nucleotide sequence.

Magnifection

Magnifection is a transient expression process that is based on expression from viral RNA replicons delivered into plant cells systemically using *Agrobacterium*. This method allows production of recombinant proteins at yields up to 5 g per kg of fresh leaf biomass, which approaches the biological limits for protein expression. Such high yields are possible because of the transient nature of the process, which allows the use of very potent amplicons derived from RNA viruses such as Tobacco mosaic virus (TMV) or Potato virus X, without limiting biomass accumulation, which takes place prior to infection. See, e.g., Marillonnet et al. (2005) *Nature Biotechnol.* 23(6):718-723.

Additional disclosure of methods and compositions for plant genetic engineering is provided in Bircher, J A (ed.) "Plant Chromosome Engineering: Methods and protocols." *Methods in Molecular Biology*, vol. 701, Springer Science+Business Media, 2011.

Transgenic Plants and Seeds

Transgenic plants derived from the plant cells can be grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) including the recombinant DNA, for example multiple plants from 2 to 20 or more transgenic events. Transgenic plants grown from transgenic seed provided herein demonstrate improved agronomic traits that contribute to increased yield or other trait that provides increased plant value, including, for example, improved seed quality. Of particular interest are plants having enhanced water use efficiency, enhanced cold tolerance, increased yield, enhanced nitrogen use efficiency, enhanced seed protein and enhanced seed oil. Transgenic plants of the include, but are not limited to, corn, soybean, cotton, canola, alfalfa, wheat, rice, sugarcane, sugar beet seed, millet, barley, peanut, pigeon pea, sorghum, vegetables (including but not limited to Broccoli, Cauliflower, Cabbage, Radish, Chinese cabbage, Melons, Watermelons, Cucumber, Gourds, Pumpkin, Squash, Pepper, Tomato, Eggplant, Onion, Carrot, Garden Bean, Sweet Corn, Pea, Dry Bean, Okra, Spinach, Leek, Lettuce, and Fennel), grape, berries (including blue, black, raspberry, mullberry, boysenberry. etc), cherry and related fruit trees (including but not limited to plum, peach, apricot, kiwi, pomegranate, mango, fig), fruit trees (including but not limited to orange, lemon, lime, blood orange, grapefruit, and the like), nut trees (including but not limited to coconut, walnut (English and black), pecan, almond, hazelnut, brazil nut, hickory nut, acorn, and the like), sunflower, other oilseed producing plants or any combinations thereof.

Plant Growth Promotion

The compositions disclosed herein, in particular, *C. subtsugae* nucleic acids and polypeptides, can be used to modulate or more particularly promote growth of plants, e.g. crops such as fruit (e.g., strawberry), vegetables (e.g., tomato, squash, pepper, eggplant), grain crops (e.g., soy, wheat, rice, corn), trees, flowers, ornamental plants, shrubs (e.g., cotton, roses), bulb plants (e.g., onion, garlic) vines (e.g., grape vine), and turf (e.g. Bermuda grass, Kentucky bluegrass, fescues). The compositions can also be used to modulate the germination of a seed(s) in a plant(s).

*C. subtsugae* nucleic acids and polypeptides, or a formulated product thereof, can be used alone or in combination with one or more other components as described below, such as growth promoting agents and/or anti-phytopathogenic agents in a tank mix or in a program (sequential application called rotation) with predetermined order and application interval during the growing season. When used in a combination with the above-mentioned products, at a concentration lower than recommended on the product label, the combined efficacy of the two or more products (one of which is the said composition disclosed herein) is, in certain embodiments, greater than the sum of each individual component's effect. Hence, the effect is enhanced by synergism between these two (or more) products, and the risk for the development of pesticide resistance among the plant pathogenic strains is reduced.

The composition can be applied by root dip at transplanting, specifically by treating a fruit or vegetable with the composition by dipping roots of the fruit or vegetable in a suspension of said composition (about 0.25 to about 1.5% and more particularly about 0.5% to about 1.0% by volume) prior to transplanting the fruit or vegetable into the soil.

Alternatively, the composition can be applied by drip or other irrigation system. Specifically, the composition can be injected into a drip irrigation system. In a particular embodiment, the composition is applied in a solution having a concentration of 1×108 CFU/mL at a rate of about 11 to about 4 quarts per acre.

In yet another embodiment, the composition can be added as an in-furrow application. Specifically, the composition can be added as an in-furrow spray at planting using nozzles calibrated to deliver a total output of 2-6 gallons/acre. Nozzles can be placed in the furrow opener on the planter so that the pesticide application and seed drop into the furrow are simultaneous.

Mixtures of the disclosed compositions with, for example, a solid or liquid adjuvant are prepared as known in the art. For example, mixtures can be prepared by homogeneously mixing and/or grinding the active ingredients with extenders such as solvents, solid carriers and, where appropriate, surface-active compounds (surfactants). The compositions can also contain additional ingredients such as stabilizers, viscosity regulators, binders, adjuvants as well as fertilizers or other active ingredients in order to obtain additional desired effects.

Combinations with Plant Growth Promoting Agents

The compositions disclosed herein can be used in combination with other growth promoting agents such as synthetic or organic fertilizers (e.g., di-ammonium phosphate, in either granular or liquid form), compost teas, seaweed extracts, plant growth hormones such as IAA (indole acetic acid) used in a rooting hormone treatment for transplants either alone or in combination with plant growth regulators such as IBA (indole butyric acid) and NAA (naphthalene acetic acid), and growth promoting microbes, such as, for example, methylotrophs, PPFM (Pink Pigmented Facultative Methylotrphs), *Bacillus* spp., *Pseudomonads, Rhizobia,* and *Trichoderma.*

Seed Treatment/Coating Agents

The compositions disclosed herein can also be used in combination with seed-coating agents. Such seed coating agents include, but are not limited to, ethylene glycol, polyethylene glycol, chitosan, carboxymethyl chitosan, peat moss, resins and waxes or chemical fungicides or bactericides with either single site, multisite or unknown mode of action.

The seed treatment methods described herein can be used in connection with any species of plant and/or the seeds thereof. In various embodiments, however, the methods are used in connection with seeds of plant species that are agronomically important, Ire particular, the seeds can be of corn, peanut, canola/rapeseed, soybean, cucurbits, crucifers, cotton, beets, rice, sorghum, sugar beet, wheat, barley, rye, sunflower, tomato, sugarcane, tobacco, oats, as well as other vegetable and leaf crops. In some embodiments, the seed is corn, soybean, or cotton seed. The seed may be a transgenic seed from which a transgenic plant can grow and incorporates a transgenic event that confers, for example, tolerance to a particular herbicide or combination of herbicides, increased disease resistance, enhanced tolerance to stress and/or enhanced yield. Transgenic seeds include, but are not limited to, seeds of corn, soybean and cotton.

Anti-Phytopathogenic Agents

The compositions disclosed herein can also be used in combination with other anti-phytopathogenic agents, such as plant extracts, biopesticides, inorganic crop protectants (such as copper), surfactants (such as rhamnolipids; Gandhi et al., 2007) or natural oils such as paraffin oil and tea tree oil possessing pesticidal properties or chemical fungicides or bactericides with either single site, multisite or unknown mode of action. As defined herein, an "anti-phytopathogenic agent" is an agent that modulates the growth of a plant pathogen, particularly a pathogen causing soil-borne disease on a plant, or alternatively prevents infection of a plant by a plant pathogen. Plant pathogens include but are not limited to fungi, bacteria, actinomycetes and viruses.

An anti-phytopathogenic agent can be a single-site antifungal agent which can include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine).

In a more particular embodiment, the antifungal agent is a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole). In a most particular embodiment, the antifungal agent is myclobutanil. In yet another particular embodiment, the antifungal agent is a quinone outside inhibitor (e.g., strobilurin). The strobilurin may include but is not limited to azoxystrobin, kresoxim-methyl or trifloxystrobin. In yet another particular embodiment, the anti-fungal agent is a quinone, e.g., quinoxyfen (5,7-dichloro-4-quinolyl 4-fluorophenyl ether).

In yet a further embodiment, the fungicide is a multi-site non-inorganic, chemical fungicide selected from the group consisting of chloronitrile, quinoxaline, sulphamide, phosphonate, phosphite, dithiocarbamate, chloralkythios, phenylpyridine-amine, and cyano-acetamide oxime.

In yet a further embodiment, the anti-phytopathogenic agent can be streptomycin, tetracycline, oxytetracycline, copper, or kasugamycin.

Bioremediation

The *C. subtsugae* genome encodes genes involved in the metabolism of, inter alia, phosphorus, iron and aromatic compounds. See, e.g., Table 6 supra. Such genes and their gene products can be used in bioremediation methods. For instance, genes and sequences related to metal transport, metal accumulation, degradation of organic compounds, and other metabolite transformation can be engineered into plants with the purpose of applying the transformed plant to bioremediation of soils, sediment, water, and other polluted substrates. Protocols for the transformation of Indian mustard (*Brassica juncea*), sunflower (*Helianthus annus*), tomato and yellow poplar (*Liriodendron tulipifera*) are known. See, e.g., Eapen and D'Souza (2005); Mello-Farias and Chavez (2008).

Plants can be transformed with Cytochrome P450-encoding genes to increase their resistance to particular pollutants, both organic and inorganic. Transformation with nucleic acids encoding enzymes involved in gluthatione conjugation (for example, glutathione S-transferases) can increase rates of xenobiotic detoxification. Plants expressing bacterial nitroreductases can be used for the detoxification of nitrate organic compounds, such as explosives.

Uses of transgenic plants for phytoremediation applications has been described, for example, by Abhilash et al. (2009); Van Aken et al. (2010); Doty (2008) and Macek et al. (2008).

Table 2 below denotes additional information of the present disclosure on *Chromobacterium substague* proteins.

TABLE 2

<table>
<tr><th>Protein name</th><th>Function</th><th>Apparent MW (SDS-PAGE)</th><th>Nucleotide sequences</th><th>Amino Acid Sequences</th><th>Homology</th></tr>
<tr><td>Scott1</td><td></td><td>~20 kDa</td><td>>fig|6666666.22288.peg.2223 [MBI-203 sp.][hypothetical protein]<br>atgtctttgactaccgattttctggagaacccgcaggctttca<br>tgcgttctcaggcgatattgattccggcgcaggttccgccc<br>ggcaacggcaaataccagttcgcggcgcagggcgcgca<br>cgcggcggtgctgcagtccaccgccgccagcccgaaca<br>tccccggtttttacgcgcatccggtggccaacaacatcaat<br>ctgttcgtgctgcccacccagcagccggcaaggtattacat<br>gttcaccgacggcatgaacggctgccagtttctggcctac<br>gggccggacaggcagcacatcaccgtcgagcacaacaa<br>cttcatcggcgacccgacgcgctacgcggcgcggctggc</td><td>MSLTTDFLENPQA<br>FMRSQAILIPAQVP<br>PGNGKYQFAAQG<br>AHAAVLQSTAASP<br>NIPGFYAHPVANN<br>INLFVLPTQQPAR<br>YYMFTDGMNGCQ<br>FLAYGPDRQHITV<br>EHNNFIGDPTRYA<br>ARLAEVVALKPA<br>YLLHISPSGVNNIP</td><td>Extracellular, Secreted.</td></tr>
</table>

TABLE 2-continued

| Protein name | Function | Apparent MW (SDS-PAGE) | Nucleotide sequences | Amino Acid Sequences | Homology |
|---|---|---|---|---|---|
| | | | ggaggtggtggcgctgaagccggcctatctgctgcatatc agcccgtcgggggtcaataacatcccggccgccaatac aacagccagcagggggtgaacatcgtcggcgaatacgg ccaggccaacggctggcgcttctgggtgcgggacagggt ggaccagaaccagggcacggtgtacgggccgctgtaa (SEQ ID NO: 4) | AGQYNSQQGVNI VGEYGQANGWRF WVRDRVDQNQGT VYGPL (SEQ ID NO: 1) | |
| Scott2 | Protease | ~20 kDa | >fig\|6666666.22288.peg.3563 [MBI-203 sp.][probable protease precursor] atggacaagagattgccagccgtggccgcggctttgctgt tggcggcttccgccgctcacgccggcgacctgcaggtca gcctggggcagccggtggtcagcgccggtcaggacgtt gacgtcgctttgacttaccgcaataccggcaaggagacctt gcacgtgtaccgctggttcgtgcccggcaaggaactgca ggagcagtttctggcggtgaatgtgaacggcaagccggc cgagtacctggggcccgcgctacaagcgtggtgccgtc gctgcgcgacaccgtggcgctggcgcccggcgccacgc tgaacgccaaggtgagggtgtccgagtattacgacctgtc caagccgggccagctgagcgtccgttttgaaagcagcag caacaaggtgctcaaccgcagcctgccggccgcgtcaa tgccaagcaggcggccgcgccgcaggccgacgaggcc atttcctccaatgtggtgggcgcctacagcgccggcagcg tcagcccttgctgaccaagtccaaggcggccaagcagg agtggcaggtgctcagccgcagcgcggtcagcggcgtc agctacgccggcaattgctcggtcagccagcagtcgcaat cgcgcgacggcgtgctggccgccagcgccatggccagc gaaacggcggcctacctggccggcacgccgtccggcac gccgcgcttcaccacttggttcggcaagtacagccaggcc aactggaccaccgccaagtcgcattacgtcaacatcaagg atgcgctggacagcaagccgatcaagctggattcagct gcaccgacggcggcacttatgcctacgtctatccggggca gccgtacaccgtctatctgtgcggcgcttctggaccgcgc cgaccaagggcaccgactccaagggcggtacccctggtg catgagttgtcgcacttcaccgtggtggcggggcacccagg accatgtctatggccaggccggcgccaagagcctggcca agagcaacccggcccaggccttggacaatgccgacaac atgaatacttcgccgagaacaccccggccagcagtaa (SEQ ID NO: 5) | MDKRLPAVAAAL LLAASAAHAGDL QVSLGQPVVSAGQ DVDVALTYRNTG KETLHVYRWFVP GKELQEQFLAVNV NGKPAEYLGPRYK RVVPSLRDTVALA PGATLNAKVRVSE YDLSKPGQLSVR FESSSNKVLNRSLP AGVNAKQAAPQ ADEAISSNVVGAY SAGSVSPLLTKSK AAKQEWQVLSRS AVSGVSYAGNCS VSQQSQSRDGVLA ASAMASETAAYL AGTPSGTPRFTTW FGKYSQANWTTA KSHYVNIKDALDS KPIKLDCSCTDGG TYAYVYPGQPYT VYLCGAFWTAPT KGTDSKGGTLVHE LSHFTVVAGTQDH VYGQAGAKSLAK SNPAQALDNADN HEYFAENTPAQQ (SEQ ID NO: 2) | Protease BLASTp C. violaceum M35 peptidase domain, Lysine-specific metallo-endopeptidase, Zn binding domain. |
| Scott3 | Metallo-protease | ~34 kDa | >fig\|6666666.22288.peg.175 [MBI-203 sp.][Vibriolysin, extracellular zinc protease (EC 3.4.24.25) @ Pseudolysin, extracellular zinc protease (EC 3.4.24.26)] atgagaaaacagcaattgatgttgcgtggtttggtcctgtcc gccctggctgtgttcagctcggcgggcgctgccgagag cgtatcgacctggaaaagctgggcaagatccaggccaac ggcgcggtggcgttcaccggcgtgaaccaggctgatctg aagccctgcgcagcacccaattcgccaccggcaaagtg gtgacccgcttccagcagtactaccagggcgtgccggtat ggggcgaagccggtggtcgaggaaaaacaggccggcgc cgtggccaagaccagcggcaaactatccggcaatacat cgccggcatccagtccgacctggcttccgccaagccgac gttgagcagcgcccaggcgttgagccaggccaaatcgct gaaggccaacggcaatcccacctacaacgagaaagccg acctagtggtgcgcctgaacgagcgcaacaccgcccagc tggtctacctagtgtccttcgtggtcgacggcaaggagccc agccgcccgcacctgatcatcgacgccaacaacggcca ggtgctgaagcagtgggaaggcctgaaccacgccgaag ccaacgcccccggcggcaacgccaagaccggcaagtat gtctacggcaccgactacggtccgctgatcgtcaccagcg attgcaagatggatagcggcaacgtcgccaccgtcaacct caacggcgtggccagcgtcaccaccccgtacaagttcg cctgcccgaccaacacctacaaagcgatcaacggcgctt actcgccgctgaacgacgcgcactacttcggcaacgtggt gttcaacctgtacaaggactggttcaacctgaagccgatca accagaagctgctgatgaaggtgcactacagccgcaact acgaaaacgcgttctgggacggcaccgcgatgaccttcg gcgacggcgccagcaccttctacccgctggtgtcgctgg acgtgtccgcgcatgaagtcagccacggcttcaccgagc agaactccggcctgtacgacggcagcggccgggca tcaacgaggcattctccgacatggccggcgaagccgccg agtactacatgaagggcaagaacgacttcctggtgggcg cggaaatcttcaagaagaccggcgcgctgcgctacttcgc cgatccgaccaaggacggccaatcgatcggcaacgcca aggactactacgacggcctggacgtgcactattccagcgg | MRKQQLMLRGLV LSALAVFSSAALA AERIDLEKLGKIQ ANGAVAFTGVNQ ADLKPLRSTQFAT GKVVTRFQQYYQ GVPVWGEAVVEE KQAGAVAKTSGK LSGQYIAGIQSDLA SAKPTLSSAQALS QAKSLKANGNPT YNEKADLVVRLN ERNTAQLVYLVSF VVDGKEPSRPHLII DANNGQVLKQWE GLNHAEANGPGG NAKTGKYVYGTD YGPLIVTSDCKMD SGNVATVNLNGG TSGTTPYKFACPT NTYKAINGAYSPL NDAHYFGNVVFN LYKDWFNLKPINQ KLLMKVHYSRNY ENAFWDGTAMTF GDGASTFYPLVSL DVSAHEVSHGFTE QNSGLVYDGQSG GINEAFSDMAGEA AEYYMKGKNDFL VGAEIFKKTGALR YFADPTKDGQSIG NAKDYYDGLDVH YSSGVYNKAFYLI ATSPNWNTRKAFE VFVDANRLYWTA | Class IV metalloprotease; vibriolysin, pseudolysin Extracellular, Zinc protease |

TABLE 2-continued

| Protein name | Function | Apparent MW (SDS-PAGE) | Nucleotide sequences | Amino Acid Sequences | Homology |
|---|---|---|---|---|---|
| | | | cgtgtacaacaaggcctttacctgatcgccaccagcccg aactggaacacccgcaaggcgtttgaagtgttcgtcgacg ccaaccggctgtactggaccgccaacgccacctacaaca gcgccgcttgcggcgtggtcaaggcggccgacgcccgc ggctacaacagcgccgacgtcaccaaggccttcaccgca gtcggcgtgacttgcaaataa (SEQ ID NO: 6) | NATYNSAACGVV KAADARGYNSAD VTKAFTAVGVTC K (SEQ ID NO: 3) | |

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

EXAMPLES

Example 1: Cell Growth and DNA Extraction

*Chromobacterium subtsugae* PRAA-1 was grown in 200 ml LB broth in 1 L flasks at 26° C. with rotation at 150 rpm for 24-48 hours. Biomass was harvested from the culture by centrifugation.

Genomic DNA was extracted using the MoBio Power Microbial Maxi-DNA Extraction Kit (MoBio Cat No. 122223-25). DNA was eluted in 1.5 ml of elution buffer (included in kit). To assess DNA quality and quantity, a 10 uL aliquot was loaded into a 1.5% agarose gel and electrophoresis was conducted for 30 minutes at 100 V. DNA was visualized with a UV transilluminator using EZ-Vision loading dye. Over 100 ug of DNA were recovered.

Example 2: DNA Sequence Determination and Assembly

DNA sequences were determined using a HiSeq 2000 (Illumina, San Diego, Calif.), with sequence reads of 100 bp, pair ended, aiming for a minimum coverage of 40×. Final data consisted of two sets of paired-end samples in FASTQ format, providing approximately 200× coverage of the genome.

The four FASTAQ files were used for assembly. FASTAQ sequences were subjected to quality control using FASTQC, and the average distance between pairs was calculated by comparing the first 10,000 pairs from both sets with the initial assembled contigs using BWA. Li & Durbin (2009) Bioinformatics 25(14):1754-1760. TrimGalore (Babraham Bioinformatics, Cambridge, UK) was then used to generate two high-quality paired-end sets and four single-read files for those sequences whose partner read was below the quality threshold of at least 50 nucleotides after clipping on Q2.

Sequence reads were assembled using Ray assembler v2.0.0. Boisvert et al. (2010) J Comput Biol. 17(11):1519-1533. A titration of kmer sizes was performed with a kmer range of 19-63; resulting in successful assemblies at 19, 21, 31, 41, 47, 49 and 63. Further scaffolding was performed using SSPACE v1.1 using all available reads on the scaffolds produced by the Ray analysis. Boetzer et al. (2011) Bioinformatics 27(4):578-579. Gaps were connected using GapFiller, with a maximum iteration of twenty steps. Boetzer & Pirovano (2012) Genome Biol. 13(6):R56. The resulting scaffolds were mapped against the reference genome of *Chromobacterium violaceum* ATCC 12742, using CONTIGuator with an e value of 1e-10. Galardini et al. (2011) Source Code Biol. Med. 6:11.

To confirm contig and scaffold orders, the alignments were inspected manually using ACT. Carver et al. (2008) Bioinformatics 24(23):2672-2676. The original dataset was mapped back onto the *Chromobacterium subtsugae* sequence using BWA (Li & Durbin, supra) with a seed length of 19.

This process yielded a high quality genome of 4,690,330 bases with a total of 145,992 bases in contigs not matching the reference genome (*Chromobacterium violaceum*) and 4,264 undefined nucleotides (N's) in 42 gaps. Subsequent filling of the gaps in pseudocontigs closed 8 of the 42 gaps and extended the pseudocontigs to 4,704,820 bases where most gaps are single 'N' positions with only 2 gaps remaining in positions 2,153,178-2,153,283 (105 bases) and 2,474,439-2,474,486 (47 bases).

Example 3: Screening of Proteins for Cabbage Loopers Insecticide Activity

Proteins Scott 1-3 (Seq ID Nos: 4-6, respectively) were fractionated by standard FPLC procedure.

Diet plates were stored in a covered container in the bioassay refrigerator (4° C.). All efficacy tests were conducted with a minimum of six dilutions and two dilution replicates (wells) per plate and a minimum of 40 wells total for each dilution. Deionized water was used as negative control. All protein candidates and the standard were serially diluted to a minimum of six dilutions. (i.e. 16%, 8%, 4%, 2%, 1% and 0.05%). Starting with the lowest dilution, 100 µL of each dilution treatment was pipetted into each well. The plate was moved into a fume hood with a small room fan. The fan was turned on and pointed at the plate in an angle that the liquid in the wells are affected by the airflow. Wells were sufficiently dry so that a neonate larva can be placed into each well without drowning. Only first through early second instar Cabbage Loopers were used for the 96-well plates. Using a fine paintbrush, single small larva was moved from its rearing area into a well. Infestation was continued until all wells have larvae in them. A small hole was made into the lid over each well for ventilation, using a dental pick or other small pointed tool. The plate was placed in a controlled-temperature chamber at 26° C., and mortality was scored on 3 to 4 days after addition of insects. Insect mortality was determined by examining the larvae in each well. Average mortality for each dilution was then determined. Tables 3-6 show the mortality of cabbage loopers achieved by the amount of Scott 1-3 (SEQ ID Nos:4-6).

TABLE 3

(Scott1; SEQ ID No: 1 or 4)

| Sample description | % mortality | | Corrected % mortality | |
|---|---|---|---|---|
| | Day 3 | Day 4 | Day 3 | Day 4 |
| Captured scott1 fraction, 0.22 mg/mL | 15.00 | 25.00 | 12.821 | 23.077 |
| Captured scott1 fraction, 0.11 mg/mL | 5.00 | 5.00 | 2.564 | 2.564 |
| Captured scott1 fraction, 0.06 mg/mL | 5.00 | 5.00 | 2.564 | 2.564 |
| Captured scott1 fraction, 0.03 mg/mL | 5.00 | 5.00 | 2.564 | 2.564 |
| Negative control (water) | 2.50 | 2.50 | | |
| Captured scott1 fraction, 0.224 mg/mL | 9.17 | 8.33 | 9.167 | 8.333 |
| Captured scott1 fraction, 0.448 mg/mL | 16.67 | 20.83 | 16.667 | 20.833 |
| Captured scott1 fraction, 0.896 mg/mL | 41.25 | 65.42 | 41.250 | 65.417 |
| Negative control (water) | 0.00 | 0.00 | | |
| Partially purified scott1, 2.9 mg/mL | 31.67 | 53.70 | 28.696 | 51.691 |
| Partially purified scott1, 5.7 mg/mL | 46.67 | 94.44 | 44.348 | 94.203 |
| Partially purified scott1, 11.5 mg/mL | 48.33 | 88.89 | 46.087 | 88.406 |
| Negative control (water) | 4.17 | 4.17 | | |

TABLE 4

(scott2; SEQ ID No: 2 or 5)

| Sample description | % mortality | | Corrected % mortality | |
|---|---|---|---|---|
| | Day 3 | Day 4 | Day 3 | Day 4 |
| Partially purified 20k protease 0.5 mg/mL | 33.33 | 33.33 | 30.43 | 30.43 |
| Partially purified 20k protease 0.5 mg/mL w/ 10 mM Zn and Ca | 55.56 | 72.22 | 53.62 | 71.01 |

TABLE 4-continued (scott2; SEQ ID No: 2 or 5)

| Sample description | % mortality | | Corrected % mortality | |
|---|---|---|---|---|
| | Day 3 | Day 4 | Day 3 | Day 4 |
| Negative control (water) | 4.17 | 4.17 | | |
| Partially purified 20 kDa protease 0.5 mg/mL w/ 10 mM Zn and Ca | 71.33 | 83.00 | 71.33 | 82.11 |
| Negative control (water) | 0.00 | 5.00 | | |
| Partially purified 20 kDa protease 0.5 mg/mL | 22.22 | 22.22 | 21.13 | 20.00 |
| Negative control (water) | 1.39 | 2.78 | | |
| Partially purified 20 kDa protease 0.5 mg/mL | 22.22 | 22.22 | 19.71 | 17.65 |
| Negative control | 3.13 | 5.56 | | |

TABLE 5

(scott3, SEQ ID No: 3 or 6)

| Sample description | % mortality | | Corrected % mortality | |
|---|---|---|---|---|
| | Day 3 | Day 4 | Day 3 | Day 4 |
| Partially purified 35 kDa protease, 0.25 mg/mL | 7.41 | 7.41 | 3.38 | 3.38 |
| Partially purified 35 kDa protease, 0.25 mg/mL w/ 10 mM Zn and Ca | 18.52 | 24.07 | 14.98 | 20.77 |
| Negative control (water) | 4.17 | 4.17 | | |
| Partially purified 35 kDa protease, 0.125 mg/mL | 0.00 | 0.00 | 0.00 | −5.26 |
| Partially purified 35 kDa protease, 0.125 mg/mL w/ 10 mM Zn and Ca | 4.00 | 6.67 | 4.00 | 1.75 |
| Negative control (water) | 0.00 | 5.00 | | |
| Partially purified 35 kDa protease 0.5 mg/mL | 74.07 | 74.07 | 73.71 | 73.33 |
| Negative control (water) | 1.39 | 2.78 | | |
| Partially purified 35 kDa protease 0.5 mg/mL | 51.85 | 57.41 | 50.30 | 54.90 |
| Negative control (water) | 3.13 | 5.56 | | |

Example 4: Transformation of Tomato (*Solanum lycopersicum*) with *Agrobacterium*

The following procedure is adapted from Sharma, M. K. et al. 2009. "A simple and efficient *Agrobacterium*-mediated procedure for transformation of tomato." Journal of Biosciences 34:423-433.

Media and Solutions

The composition of various media is described in Table 6. Media components, except agar, are combined according to Table 6 and adjusted to pH 5.8 using 1N KOH, before adding plant-tissue culture grade agar. Stock solutions of BAP (6-benzylmaino purine) and zeatin are prepared in dimethyl sulphoxide (DMSO). Antibiotic stock solutions are prepared in deionized water and filter-sterilized. *Agrobacterium* strain AGL1 is grown on YEM agar or broth containing 100 mg/l rifampicin and 50 mg/l kanamycin.

Preparation of *Agrobacterium*

*Agrobacterium tumefaciens*, transformed with the gene or genes of interest, (e.g., any of the genes disclosed in SEQ ID NOs:1-6) is grown in YEM medium with rifampicin and kanamycin, in shaking culture for 72 h at 28° C. and 200 rpm. Cells are pelleted by centrifugation, washed and re-suspended in WS medium. Bacterial density is determined by measuring OD600 and the final cell concentration is adjusted to ~108 cells/ml by diluting with WS medium.

Plant Transformation

Middle pieces (0.7×1.0 cm) from 10-day cotyledons are collected by excising at the tip and base. The sections are pre-cultured for 48 hours at 28° C. on M1 medium, with the adaxias surface in direct contact with the medium.

Healthy explants are selected and incubated in *Agrobacterium* suspension for 30 minutes, with inversion every 10 minutes. Explants are blotted on sterile tissue paper and returned to M1 agar (50-80 explants per plate) for an additional 72 hours. The explants are then washed 4-5 times in WS medium, blotted on sterile tissue paper and transferred to SM containing 1 mg/L trans-zeatin for regeneration (20-25 explants per regeneration plate).

Regeneration plates are incubated at 28° C. under a 16/8 light/dark cycle. Regeneration is evidenced by development of a callus. Regenerated explants are selected and transferred to fresh SM medium every 15 days.

Regenerated shoots can be excised from the callus and transferred to RM medium.

Plantlets that are at least 2 inches in height and have strong roots are selected for transfer to pots. Planting substrate consists of potting soil mixed 1:1 with 1:1:1 vermiculite: perlite: sphagnum.

TABLE 6

| | M1 | M2 | WS | SM | RM |
|---|---|---|---|---|---|
| MS Salts (Murashige and Skoog, 1962) | 0.5x | 1x | 1x | 1x | 1x |
| Gamborg's B5 vitamins | 0.5x | 1x | 1x | 1x | 1x |
| Sucrose (g/L) | 15 | 30 | 30 | 30 | 30 |
| Agar (% w/v) | 0.8 | 0.8 | 0 | 0.8 | 0.8 |
| BAP (mg/L) | 0 | 2 | 0 | 0 | 0 |
| Kanamycin (mg/L) | 0 | 0 | 0 | 100 | 100 |
| Cefotaxime (mg/L) | 0 | 0 | 0 | 500 | 500 |

Example 5: Creation of Transgenic Soybean Plants Comprising an Insecticidal Gene from *Chromobacterium substugae*

Mature *glycine max* seeds are surface sterilized with chlorine gas inside a bell jar under a fume hood. Seeds are kept in 100×20 mm Petri dishes with chlorine gas produced by pouring 100 ml of 4% sodium hypochlorite into a beaker and adding 5 ml of 12N hydrochloric acid. After sterilization, seeds are placed on germination medium (GM; MS basal salts with vitamins, 3% sucrose, 0.8% plant agar, and 1 mg/L BAP, optimized from regeneration experiment, pH 5.8). Murashige and Skoog, 1962. Seeds are germinated under fluorescent light or darkness at 24±1° C. for 5-7 days to compare transformation frequency.

The method described here is a modification of that described by Zhang et al. (1999) *Plant Cell, Tissue and Organ Culture* 56:37-46. Two cotyledonary explants are obtained by cutting a horizontal slice through the hypocotyl with a No. 11 surgical blade. The hypocotyl is subsequently removed and ten scratches are made at the surface of cotyledonary node regions. Explants are immersed for 30 min in a suspension of *A. tumefaciens* which has been engineered to comprise the gene of interest, e.g., a gene that encodes an insecticidal protein, or a protein that is involved in the synthesis of an insecticidal compound. See Tables 2 above for listings of exemplary genes of interest. Following immersion, ten explants are randomly placed on sterile filter paper placed on solid co-cultivation medium (CM; Gamborg's B5 basal salts with vitamins, 3% sucrose, 20 mM MES, 3.3 mM L-cysteine, 1 mM dithiothreitol, 0.1 mM acetosyringone, 0.8% plant agar, pH 5.4) (Gamborg et al., 1968) in 100×20 mm Petri dishes, and incubated at 24±1° C. for 5 days under dark conditions.

After 5 days of co-cultivation, explants are briefly washed in liquid shoot induction medium (SIM; Gamborg's B5 basal salts with vitamins, 3% sucrose, 3 mM MES, 1.67 mg/L BAP, 250 mg/L cefotaxime, pH 5.7) to remove excess *A. tumefaciens* on explants. Explants are then transferred to solidified SIM without PPT to stimulate shoot induction for the first 14 days, after which the explants are sub-cultured on fresh SIM containing 5 mg/L PPT for selection of transformed shoots. Organogenic shoots from the explants are trimmed and then transferred to shoot elongation medium (SEM; MS basal salts with vitamins, 3% sucrose, 3 mM MES, 0.5 mg/L giberellic acid, 50 mg/L asparagine, 1 mg/L zeatin, 0.1 mg/L indole-3-acetic acid, 250 mg/L cefotaxime, 50 mg/L vancomycin, 0.8% plant agar, 5 mg/L PPT, pH 5.7). Explants are transferred to new SEM medium every 14 days, and surviving shoots are planted on root induction medium (RIM; MS basal salts with vitamins, 3% sucrose, 1 mg/L naphthalene acetic acid, 0.8% plant agar, pH 5.7) and grown until roots develop. After acclimation, the transgenic plants are transplanted to potting soil and maintained in a greenhouse. Selection is carried out by PCR. See also Lee, et al. (2011) *J. of Korean Soc. Appl. Biol. Chem.* 54: 37-45.

Example 6: Screening of Proteins for Cabbage Loopers (*Trichoplusia ni*) (CL), *Lygus* (*Lygus hesperus*), Beet Armyworms (*Spodoptera exigua*) (BAW), and Diamondback Moth (*Plutella xylostella*) (DBM) Insecticidal Activity Proteins were partially purified by strong cation exchange and hydrophobic interaction chromatography. Protein concentration was estimated using the Invitrogen Quant-iT or Qubit assay calibrated with BSA. Unless otherwise noted, scott1 (SEQ ID NO:1 or 4) was submitted for bioassay at 5 mg/mL, scott2 (SEQ ID NO:2 or 5) at 1 mg/mL, and scott3 (SEQ ID NO:3 or 6) at 1 mg/mL total protein amounts. Proteins were buffered at pH 6 in 20 mM MES or pH 7.5 with 20 mM Tris. Scott2 was spiked with up to 5 mM ZnCl, and CaCl.

Activity against Cabbage Loopers (repeated as compared to example 3), Beet Armyworm and Diamondback Moth was tested on Diet Overlay Bioassays. The appropriate artificial insect diet was dispensed into each well of a standard 96 well plate and allowed to dry. Once the diet solidified, 100 uL of the treatment was pipetted into the appropriate number of wells and allowed to dry. A single 1st instar larva was delivered into each well of a 96 well plate. Mortality was scored at 4 days after treatment.

Activity against *lygus* was tested on an Artificial Diet Bioassay as follows: Diet packets were prepared by combining the appropriate amount of *lygus* artificial diet and stock treatment solution. The mixtures were vortexed and distributed evenly amongst the diet packets. Nymphs, 10-12 lygus 2nd or 3rd instar, were placed into a petri dish, covered with a mesh lid and sealed with Parafilm. Mortality was scored at 4 days after exposure to the treated diet.

Efficacy is expressed as percentage mortality at 4 days post treatment. Results (in duplicates) in % mortality are shown in Table 7. Scott1 was prepared at 4.9 mg/mL for the first *lygus* assay. Scott3 was prepared at 0.42 mg/mL for the first *lygus* assay and at 0.82 mg/mL for the first cabbage looper assay.

TABLE 7

| | CL % Mortality | | Lygus | | BAW | | DBM | |
|---|---|---|---|---|---|---|---|---|
| Scott1 | 90.91 | 100 | 21.98 | 12.5 | 8.33 | 0 | 95.83 | 77.08 |
| Scott2 | 100 | 92.86 | 22.88 | 19.3 | 25 | 33.33 | 58.33 | 95.83 |
| Scott3 | 63.64 | 100 | 7.54 | 15.21 | 29.17 | 33.33 | 95.83 | 70.83 |

The inventions described and claimed herein are not to be limited in scope by the specific aspects herein disclosed, since these aspects are intended to be illustrative. Any equivalent aspects are intended to be within the scope of the disclosure. Indeed, various modifications of the methods and compositions shown and described herein will be apparent to those skilled in the art from the foregoing description. Such modifications are also intended to fall within the scope of the appended claims. In the case of conflict, the present disclosure including definitions will control.

What is claimed is:

1. A cell comprising a recombinant vector having a heterologous promoter operably linked to a nucleic acid sequence encoding a polypeptide with 100% identity to SEQ ID NO: 2.

2. A plant or plant parts comprising one or more cells according to claim 1 or progeny or seed thereof.

3. The plant or plant parts of claim 2, wherein said plant part is selected from the group consisting of pollen, ovule, flower, shoot, root, stalk, silk, tassel, ear, and leaf tissue.

4. The cell of claim 1, wherein said cell is a bacterial, mammalian, or fungal cell.

5. A method of producing an insect resistant plant comprising the step of transforming a recombinant vector having a heterologous promoter operably linked to a nucleic acid sequence encoding a polypeptide with 100% identity to SEQ ID NO: 2 into a plant cell.

6. Anti-counterfeit milled seed having, as an indication of origin, a plant cell of claim 1.

* * * * *

```
                    SEQUENCE LISTING

<160> NUMBER OF SEQ ID NOS: 6

<210> SEQ ID NO 1
<211> LENGTH: 183
<212> TYPE: PRT
<213> ORGANISM: chromobacterium subtsugae

<400> SEQUENCE: 1

Met Ser Leu Thr Thr Asp Phe Leu Glu Asn Pro Gln Ala Phe Met Arg
1               5                   10                  15

Ser Gln Ala Ile Leu Ile Pro Ala Gln Val Pro Pro Gly Asn Gly Lys
            20                  25                  30

Tyr Gln Phe Ala Ala Gln Gly Ala His Ala Ala Val Leu Gln Ser Thr
        35                  40                  45

Ala Ala Ser Pro Asn Ile Pro Gly Phe Tyr Ala His Pro Val Ala Asn
    50                  55                  60

Asn Ile Asn Leu Phe Val Leu Pro Thr Gln Gln Pro Ala Arg Tyr Tyr
65                  70                  75                  80

Met Phe Thr Asp Gly Met Asn Gly Cys Gln Phe Leu Ala Tyr Gly Pro
                85                  90                  95

Asp Arg Gln His Ile Thr Val Glu His Asn Asn Phe Ile Gly Asp Pro
            100                 105                 110

Thr Arg Tyr Ala Ala Arg Leu Ala Glu Val Val Ala Leu Lys Pro Ala
        115                 120                 125

Tyr Leu Leu His Ile Ser Pro Ser Gly Val Asn Asn Ile Pro Ala Gly
    130                 135                 140

Gln Tyr Asn Ser Gln Gln Gly Val Asn Ile Val Gly Glu Tyr Gly Gln
145                 150                 155                 160

Ala Asn Gly Trp Arg Phe Trp Val Arg Asp Arg Val Asp Gln Asn Gln
                165                 170                 175

Gly Thr Val Tyr Gly Pro Leu
            180

<210> SEQ ID NO 2
<211> LENGTH: 364
<212> TYPE: PRT
<213> ORGANISM: chromobacterium subtsugae

<400> SEQUENCE: 2

Met Asp Lys Arg Leu Pro Ala Val Ala Ala Ala Leu Leu Leu Ala Ala
1               5                   10                  15

Ser Ala Ala His Ala Gly Asp Leu Gln Val Ser Leu Gly Gln Pro Val
            20                  25                  30

Val Ser Ala Gly Gln Asp Val Asp Val Ala Leu Thr Tyr Arg Asn Thr
        35                  40                  45
```

```
Gly Lys Glu Thr Leu His Val Tyr Arg Trp Phe Val Pro Gly Lys Glu
    50                  55                  60

Leu Gln Glu Gln Phe Leu Ala Val Asn Val Asn Gly Lys Pro Ala Glu
65                  70                  75                  80

Tyr Leu Gly Pro Arg Tyr Lys Arg Val Val Pro Ser Leu Arg Asp Thr
                85                  90                  95

Val Ala Leu Ala Pro Gly Ala Thr Leu Asn Ala Lys Val Arg Val Ser
            100                 105                 110

Glu Tyr Tyr Asp Leu Ser Lys Pro Gly Gln Leu Ser Val Arg Phe Glu
        115                 120                 125

Ser Ser Ser Asn Lys Val Leu Asn Arg Ser Leu Pro Ala Gly Val Asn
    130                 135                 140

Ala Lys Gln Ala Ala Ala Pro Gln Ala Asp Glu Ala Ile Ser Ser Asn
145                 150                 155                 160

Val Val Gly Ala Tyr Ser Ala Gly Ser Val Ser Pro Leu Leu Thr Lys
                165                 170                 175

Ser Lys Ala Ala Lys Gln Glu Trp Gln Val Leu Ser Arg Ser Ala Val
            180                 185                 190

Ser Gly Val Ser Tyr Ala Gly Asn Cys Ser Val Ser Gln Gln Ser Gln
        195                 200                 205

Ser Arg Asp Gly Val Leu Ala Ala Ser Ala Met Ala Ser Glu Thr Ala
    210                 215                 220

Ala Tyr Leu Ala Gly Thr Pro Ser Gly Thr Pro Arg Phe Thr Thr Trp
225                 230                 235                 240

Phe Gly Lys Tyr Ser Gln Ala Asn Trp Thr Thr Ala Lys Ser His Tyr
                245                 250                 255

Val Asn Ile Lys Asp Ala Leu Asp Ser Lys Pro Ile Lys Leu Asp Cys
            260                 265                 270

Ser Cys Thr Asp Gly Gly Thr Tyr Ala Tyr Val Tyr Pro Gly Gln Pro
        275                 280                 285

Tyr Thr Val Tyr Leu Cys Gly Ala Phe Trp Thr Ala Pro Thr Lys Gly
    290                 295                 300

Thr Asp Ser Lys Gly Gly Thr Leu Val His Glu Leu Ser His Phe Thr
305                 310                 315                 320

Val Val Ala Gly Thr Gln Asp His Val Tyr Gly Gln Ala Gly Ala Lys
                325                 330                 335

Ser Leu Ala Lys Ser Asn Pro Ala Gln Ala Leu Asp Asn Ala Asp Asn
            340                 345                 350

His Glu Tyr Phe Ala Glu Asn Thr Pro Ala Gln Gln
        355                 360

<210> SEQ ID NO 3
<211> LENGTH: 489
<212> TYPE: PRT
<213> ORGANISM: chromobacterium subtsugae

<400> SEQUENCE: 3

Met Arg Lys Gln Gln Leu Met Leu Arg Gly Leu Val Leu Ser Ala Leu
1               5                   10                  15

Ala Val Phe Ser Ser Ala Ala Leu Ala Ala Glu Arg Ile Asp Leu Glu
            20                  25                  30

Lys Leu Gly Lys Ile Gln Ala Asn Gly Ala Val Ala Phe Thr Gly Val
        35                  40                  45

Asn Gln Ala Asp Leu Lys Pro Leu Arg Ser Thr Gln Phe Ala Thr Gly
```

```
                50                  55                  60
Lys Val Thr Arg Phe Gln Gln Tyr Tyr Gln Gly Val Pro Val Trp
 65                  70                  75                  80

Gly Glu Ala Val Val Glu Glu Lys Gln Ala Gly Ala Val Ala Lys Thr
                         85                  90                  95

Ser Gly Lys Leu Ser Gly Gln Tyr Ile Ala Gly Ile Gln Ser Asp Leu
                100                 105                 110

Ala Ser Ala Lys Pro Thr Leu Ser Ser Ala Gln Ala Leu Ser Gln Ala
                115                 120                 125

Lys Ser Leu Lys Ala Asn Gly Asn Pro Thr Tyr Asn Glu Lys Ala Asp
                130                 135                 140

Leu Val Val Arg Leu Asn Glu Arg Asn Thr Ala Gln Leu Val Tyr Leu
145                 150                 155                 160

Val Ser Phe Val Val Asp Gly Lys Glu Pro Ser Arg Pro His Leu Ile
                    165                 170                 175

Ile Asp Ala Asn Asn Gly Gln Val Leu Lys Gln Trp Glu Gly Leu Asn
                180                 185                 190

His Ala Glu Ala Asn Gly Pro Gly Gly Asn Ala Lys Thr Gly Lys Tyr
                195                 200                 205

Val Tyr Gly Thr Asp Tyr Gly Pro Leu Ile Val Thr Ser Asp Cys Lys
210                 215                 220

Met Asp Ser Gly Asn Val Ala Thr Val Asn Leu Asn Gly Gly Thr Ser
225                 230                 235                 240

Gly Thr Thr Pro Tyr Lys Phe Ala Cys Pro Thr Asn Thr Tyr Lys Ala
                245                 250                 255

Ile Asn Gly Ala Tyr Ser Pro Leu Asn Asp Ala His Tyr Phe Gly Asn
                260                 265                 270

Val Val Phe Asn Leu Tyr Lys Asp Trp Phe Asn Leu Lys Pro Ile Asn
                275                 280                 285

Gln Lys Leu Leu Met Lys Val His Tyr Ser Arg Asn Tyr Glu Asn Ala
                290                 295                 300

Phe Trp Asp Gly Thr Ala Met Thr Phe Gly Asp Gly Ala Ser Thr Phe
305                 310                 315                 320

Tyr Pro Leu Val Ser Leu Asp Val Ser Ala His Glu Val Ser His Gly
                325                 330                 335

Phe Thr Glu Gln Asn Ser Gly Leu Val Tyr Asp Gly Gln Ser Gly Gly
                340                 345                 350

Ile Asn Glu Ala Phe Ser Asp Met Ala Gly Glu Ala Ala Glu Tyr Tyr
                355                 360                 365

Met Lys Gly Lys Asn Asp Phe Leu Val Gly Ala Glu Ile Phe Lys Lys
370                 375                 380

Thr Gly Ala Leu Arg Tyr Phe Ala Asp Pro Thr Lys Asp Gly Gln Ser
385                 390                 395                 400

Ile Gly Asn Ala Lys Asp Tyr Asp Gly Leu Asp Val His Tyr Ser
                405                 410                 415

Ser Gly Val Tyr Asn Lys Ala Phe Tyr Leu Ile Ala Thr Ser Pro Asn
                420                 425                 430

Trp Asn Thr Arg Lys Ala Phe Glu Val Phe Val Asp Ala Asn Arg Leu
                435                 440                 445

Tyr Trp Thr Ala Asn Ala Thr Tyr Asn Ser Ala Ala Cys Gly Val Val
                450                 455                 460

Lys Ala Ala Asp Ala Arg Gly Tyr Asn Ser Ala Asp Val Thr Lys Ala
465                 470                 475                 480
```

Phe Thr Ala Val Gly Val Thr Cys Lys
485

<210> SEQ ID NO 4
<211> LENGTH: 552
<212> TYPE: DNA
<213> ORGANISM: chromobacterium subtsugae

<400> SEQUENCE: 4
atgtctttga ctaccgattt tctggagaac ccgcaggctt tcatgcgttc tcaggcgata 60
ttgattccgg cgcaggttcc gcccggcaac ggcaaatacc agttcgcggc gcagggcgcg 120
cacgcggcgg tgctgcagtc caccgccgcc agcccgaaca tccccggttt ttacgcgcat 180
ccggtggcca acaacatcaa tctgttcgtg ctgcccaccc agcagccggc aaggtattac 240
atgttcaccg acggcatgaa cggctgccag tttctggcct acgggccgga caggcagcac 300
atcaccgtcg agcacaacaa cttcatcggc gacccgacgc gctacgcggc gcggctggcg 360
gaggtggtgg cgctgaagcc ggcctatctg ctgcatatca gcccgtcggg ggtcaataac 420
atcccggccg gccaatacaa cagccagcag gggggtgaaca tcgtcggcga atacggccag 480
gccaacggct ggcgcttctg ggtgcgggac agggtggacc agaaccaggg cacggtgtac 540
gggccgctgt aa 552

<210> SEQ ID NO 5
<211> LENGTH: 1095
<212> TYPE: DNA
<213> ORGANISM: chromobacterium subtsugae

<400> SEQUENCE: 5
atggacaaga gattgccagc cgtggccgcg gctttgctgt tggcggcttc cgccgctcac 60
gccggcgacc tgcaggtcag cctggggcag ccggtggtca gcgcgggtca ggacgttgac 120
gtcgctttga cttaccgcaa taccggcaag gagaccttgc acgtgtaccg ctggttcgtg 180
cccggcaagg aactgcagga gcagtttctg gcggtgaatg tgaacggcaa gccggccgag 240
tacctgggcc cgcgctacaa gcgcgtggtg ccgtcgctgc gcgacaccgt ggcgctggcg 300
cccggcgcca cgctgaacgc caaggtgagg gtgtccgagt attacgacct gtccaagccg 360
ggccagctga gcgtccgttt tgaaagcagc agcaacaagg tgctcaaccg cagcctgccg 420
gccggcgtca atgccaagca ggcggccgcg ccgcaggccg acgaggccat ttcctccaat 480
gtggtgggcg cctacagcgc cggcagcgtc agccccttgc tgaccaagtc caaggcggcc 540
aagcaggagt ggcaggtgct cagccgcagc gcggtcagcg gcgtcagcta cgccggcaat 600
tgctcggtca gccagcagtc gcaatcgcgc gacggcgtgc tggccgccag cgccatggcc 660
agcgaaacgg cggcctacct ggccggcacg ccgtccggca cgccgcgctt caccacttgg 720
ttcggcaagt acagccaggc caactggacc accgccaagt cgcattacgt caacatcaag 780
gatgcgctgg acagcaagcc gatcaagctg gattgcagct gcaccgacgg cggcacttat 840
gcctacgtct atccggggca gccgtacacc gtctatctgt gcggcgcttt ctggaccgcg 900
ccgaccaagg gcaccgactc caagggcggc accctggtgc atgagttgtc gcacttcacc 960
gtggtggcgg gcacccagga ccatgtctat ggccaggccg gcgccaagag cctggccaag 1020
agcaacccgg cccaggcctt ggacaatgcc gacaaccatg aatacttcgc cgagaacacc 1080
ccggcgcagc agtaa 1095

-continued

```
<210> SEQ ID NO 6
<211> LENGTH: 1470
<212> TYPE: DNA
<213> ORGANISM: chromobacterium subtsugae

<400> SEQUENCE: 6
atgagaaaac agcaattgat gttgcgtggt ttggtcctgt ccgccctggc tgtgttcagc     60
tcggcggcgc tggcggccga gcgtatcgac ctggaaaagc tgggcaagat ccaggccaac    120
ggcgcggtgg cgttcaccgg cgtgaaccag gctgatctga agcccctgcg cagcacccaa    180
ttcgccaccg gcaaagtggt gacccgcttc cagcagtact accagggcgt gccggtatgg    240
ggcgaagccg tggtcgagga aaaacaggcc ggcgccgtgg ccaagaccag cggcaaacta    300
tccggccaat acatcgccgg catccagtcc gacctggctt ccgccaagcc gacgttgagc    360
agcgcccagg cgttgagcca ggccaaatcg ctgaaggcca acggcaatcc cacctacaac    420
gagaaagccg acctagtggt gcgcctgaac gagcgcaaca ccgcccagct ggtctaccta    480
gtgtccttcg tggtcgacgg caaggagccc agccgcccgc acctgatcat cgacgccaac    540
aacggccagg tgctgaagca gtgggaaggc ctgaaccacg ccgaagccaa cggccccggc    600
ggcaacgcca agaccggcaa gtatgtctac ggcaccgact acggtccgct gatcgtcacc    660
agcgattgca agatggatag cggcaacgtc gccaccgtca acctcaacgg cggcaccagc    720
ggcaccaccc cgtacaagtt cgcctgcccg accaacacct acaaagcgat caacggcgct    780
tactcgccgc tgaacgacgc gcactacttc ggcaacgtgg tgttcaacct gtacaaggac    840
tggttcaacc tgaagccgat caaccagaag ctgctgatga aggtgcacta cagccgcaac    900
tacgaaaacg cgttctggga cggcaccgcg atgaccttcg gcgacggcgc cagcaccttc    960
tacccgctgg tgtcgctgga cgtgtccgcg catgaagtca gccacggctt caccgagcag   1020
aactccggcc tggtctacga cggccagtcc ggcggcatca acgaggcatt ctccgacatg   1080
gccggcgaag ccgccgagta ctacatgaag ggcaagaacg acttcctggt gggcgcggaa   1140
atcttcaaga agaccggcgc gctgcgctac ttcgccgatc cgaccaagga cggccaatcg   1200
atcggcaacg ccaaggacta ctacgacggc ctggacgtgc actattccag cggcgtgtac   1260
aacaaggcct tttacctgat cgccaccagc ccgaactgga acacccgcaa ggcgtttgaa   1320
gtgttcgtcg acgccaaccg gctgtactgg accgccaacg ccacctacaa cagcgccgct   1380
tgcggcgtgg tcaaggcggc cgacgcccgc ggctacaaca gcgccgacgt caccaaggcc   1440
ttcaccgcag tcggcgtgac ttgcaaataa                                    1470
```